US010149788B2

(12) United States Patent
Kreuzer et al.

(10) Patent No.: US 10,149,788 B2
(45) Date of Patent: *Dec. 11, 2018

(54) DISPOSABLE DIAPERS

(75) Inventors: Carsten Heinrich Kreuzer, Hofheim (DE); Rodrigo Rosati, Frankfurt am Main (DE); Blanca Arizti, Frankfurt am Main (DE); Hans Adolf Jackels, Mechernich (DE); Ernesto G. Bianchi, Oberursel (DE); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 467 days.

This patent is subject to a terminal disclaimer.

(21) Appl. No.: 13/491,644

(22) Filed: Jun. 8, 2012

(65) Prior Publication Data

US 2012/0316528 A1 Dec. 13, 2012

Related U.S. Application Data

(60) Provisional application No. 61/495,406, filed on Jun. 10, 2011.

(51) Int. Cl.
*A61F 13/534* (2006.01)
*A61F 13/533* (2006.01)
*A61F 13/536* (2006.01)
*A61F 13/53* (2006.01)

(52) U.S. Cl.
CPC ......... *A61F 13/534* (2013.01); *A61F 13/533* (2013.01); *A61F 13/536* (2013.01); *A61F 2013/530343* (2013.01); *A61F 2013/530408* (2013.01); *A61F 2013/530868* (2013.01)

(58) Field of Classification Search
CPC .............. A61F 13/532; A61F 13/535; A61F 2013/530554; A61F 13/49001; A61F 2013/530875
USPC .................................................. 604/365, 366
See application file for complete search history.

(56) References Cited

U.S. PATENT DOCUMENTS

| | | | |
|---|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |

(Continued)

FOREIGN PATENT DOCUMENTS

| | | |
|---|---|---|
| CA | 2001370 | 4/1990 |
| CA | 2291997 | 6/2000 |

(Continued)

OTHER PUBLICATIONS

U.S. Appl. No. 13/491,642, filed Jun. 8, 2012, Rosati, et al.
U.S. Appl. No. 13/491,643, filed Jun. 8, 2012, Rosati, et al.
U.S. Appl. No. 13/491,648, filed Jun. 8, 2012, Kreuzer, et al.

*Primary Examiner* — Paula L Craig
(74) *Attorney, Agent, or Firm* — Wednesday G. Shipp

(57) ABSTRACT

Disposable absorbent diapers are provided with improved comfort, fit and liquid transportation. The absorbent core of the disposable absorbent diapers includes at least one absorbent structure comprising a substrate layer and an absorbent layer with channels.

11 Claims, 11 Drawing Sheets

(56) References Cited

U.S. PATENT DOCUMENTS

| | | | |
|---|---|---|---|
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Van Norden |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,343,543 A * | 9/1967 | Glassman ......... A61F 13/47227 604/372 |
| 3,386,442 A | 6/1968 | Sabee |
| 3,411,504 A | 11/1968 | Glassman |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,287,153 A | 9/1981 | Towsend |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,840,692 A * | 6/1989 | Kamstrup-Larsen ...... A61F 5/4401 156/252 |

(56) References Cited

U.S. PATENT DOCUMENTS

| | | |
|---|---|---|
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,188,624 A | 2/1993 | Young et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,053 A * | 4/1994 | Genaro ............ A61F 13/49007 604/378 |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,246 A * | 1/1995 | Kawano ............... A61F 13/494 604/358 |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,458,592 A * | 10/1995 | Abuto .................. A61F 13/531 156/167 |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,487,736 A | 1/1996 | Phan |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,575,783 A | 11/1996 | Clear et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A * | 1/1997 | Tanzer et al. ................. 604/368 |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |

(56) References Cited

U.S. PATENT DOCUMENTS

| | | |
|---|---|---|
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |
| 5,607,416 A | 5/1997 | Yamamoto et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,300 A | 10/1997 | Ahr |
| 5,683,374 A | 11/1997 | Yamamoto |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,713,881 A | 2/1998 | Rezai et al. |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A * | 12/1998 | Fujioka ............. A61F 13/515 604/380 |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,964,743 A | 10/1999 | Abuto et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,010,490 A | 1/2000 | Freeland et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,261,679 B1 | 7/2001 | Chen et al. |
| 6,264,639 B1 | 7/2001 | Sauer |
| 6,265,488 B1 | 7/2001 | Fujino et al. |
| 6,290,686 B1 | 9/2001 | Tanzer et al. |
| 6,293,933 B1 * | 9/2001 | Ahlstrand ......... A61F 13/49446 604/378 |
| 6,306,122 B1 | 10/2001 | Narawa et al. |

(56) References Cited

U.S. PATENT DOCUMENTS

| | | | |
|---|---|---|---|
| 6,307,119 B1 | 10/2001 | Cammarota et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,590,138 B2 * | 7/2003 | Onishi .................. A61F 13/532 604/378 |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B2 | 5/2004 | Graef |
| 6,746,976 B1 | 6/2004 | Urankar et al. |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |

(56) References Cited

U.S. PATENT DOCUMENTS

| | | |
|---|---|---|
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| RE39,919 E | 11/2007 | Dodge, II et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,520,874 B2 * | 4/2009 | Koyama ............ A61F 13/49017 604/385.01 |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,844 B2 | 5/2010 | Olson |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,956,236 B2 | 6/2011 | Ponomarenko et al. |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,030,536 B2 | 10/2011 | Ponomarenko et al. |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,282,617 B2 | 10/2012 | Kaneda |
| 8,283,516 B2 | 10/2012 | Litvay |
| 8,317,766 B2 | 11/2012 | Naoto |

(56) References Cited

U.S. PATENT DOCUMENTS

| | | |
|---|---|---|
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |
| 8,361,047 B2 | 1/2013 | Mukai |
| 8,377,025 B2 | 2/2013 | Nakajima |
| 8,450,555 B2 | 5/2013 | Nahn et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sprerl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,326,896 B2 | 5/2016 | Schaefer et al. |
| 9,468,566 B2 * | 10/2016 | Rosati .................. A61F 13/535 |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan et al. |
| 2002/0087139 A1 | 7/2002 | Popp et al. |
| 2002/0095126 A1 | 7/2002 | Inoue et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0115972 A1 | 8/2002 | Dabi et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0088229 A1 * | 5/2003 | Baker ................ A61F 13/53717 604/385.101 |
| 2003/0105190 A1 | 6/2003 | Diehl et al. |
| 2003/0109839 A1 | 6/2003 | Costae et al. |
| 2003/0114811 A1 | 6/2003 | Christen et al. |
| 2003/0114816 A1 | 6/2003 | Underhill et al. |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee et al. |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064113 A1 | 4/2004 | Erdman |
| 2004/0064115 A1 | 4/2004 | Arora |
| 2004/0064116 A1 | 4/2004 | Arora |
| 2004/0064125 A1 | 4/2004 | Justmann |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127135 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0214499 A1 | 10/2004 | Qin et al. |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0101929 A1 | 5/2005 | Waksmundzki et al. |
| 2005/0137543 A1 | 6/2005 | Underhill et al. |
| 2005/0148258 A1 | 7/2005 | Chakravarty |
| 2005/0148961 A1 | 7/2005 | Sosalla et al. |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0217791 A1 | 10/2005 | Costello et al. |
| 2005/0229543 A1 | 10/2005 | Tippey |
| 2005/0234414 A1 | 10/2005 | Liu et al. |
| 2005/0245684 A1 | 11/2005 | Daniel et al. |
| 2005/0288645 A1 | 12/2005 | LaVon |
| 2005/0288646 A1 | 12/2005 | LaVon |

(56) References Cited

U.S. PATENT DOCUMENTS

| | | |
|---|---|---|
| 2006/0004334 A1* | 1/2006 | Schlinz et al. ............... 604/366 |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torii et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof et al. |
| 2007/0044903 A1 | 3/2007 | Wisneski et al. |
| 2007/0049892 A1 | 3/2007 | Lord et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0106013 A1 | 5/2007 | Adachi et al. |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0239125 A9 | 10/2007 | Erdman et al. |
| 2007/0244455 A1* | 10/2007 | Hansson ............ A61F 13/4704 604/385.201 |
| 2007/0246147 A1 | 10/2007 | Venturino et al. |
| 2007/0255245 A1 | 11/2007 | Asp et al. |
| 2007/0282288 A1 | 12/2007 | Noda |
| 2007/0282290 A1 | 12/2007 | Cole |
| 2007/0282291 A1 | 12/2007 | Cole |
| 2007/0287971 A1 | 12/2007 | Roe et al. |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0208154 A1 | 8/2008 | Oetjen et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1* | 12/2008 | Hundorf et al. ............... 604/366 |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | Macdonald |
| 2009/0157027 A1* | 6/2009 | Kamphus ............... A61L 15/26 604/365 |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2009/0326494 A1 | 12/2009 | Uchida et al. |
| 2009/0326497 A1 | 12/2009 | Schmidt |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii |
| 2010/0274210 A1 | 10/2010 | Noda |
| 2010/0305537 A1* | 12/2010 | Ashton ............ A61F 13/49001 604/374 |
| 2010/0312208 A1 | 12/2010 | Bond et al. |
| 2010/0324521 A1 | 12/2010 | Mukai |
| 2010/0324523 A1 | 12/2010 | Mukai |
| 2011/0034603 A1 | 2/2011 | Fujino et al. |
| 2011/0041999 A1 | 2/2011 | Hundorf et al. |
| 2011/0046592 A1 | 2/2011 | Nishikawa et al. |
| 2011/0060301 A1 | 3/2011 | Nishikawa et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0196330 A1 | 8/2011 | Hammons et al. |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |

(56) References Cited

U.S. PATENT DOCUMENTS

| | | |
|---|---|---|
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0175056 A1 | 7/2012 | Tsang |
| 2012/0184934 A1 | 7/2012 | Venturino |
| 2012/0220972 A1 | 8/2012 | Kawamura et al. |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1* | 12/2012 | Rosati .................. A61F 13/532 604/366 |
| 2012/0316529 A1* | 12/2012 | Kreuzer ................ A61F 13/533 604/366 |
| 2012/0316530 A1 | 12/2012 | Hundorf et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2013/0240125 A1 | 9/2013 | Nelson et al. |
| 2013/0310784 A1 | 11/2013 | Bryant et al. |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby et al. |
| 2014/0121625 A1 | 5/2014 | Kirby et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0299815 A1 | 10/2014 | Ueda et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2014/0371701 A1 | 12/2014 | Bianchi et al. |
| 2015/0038931 A1* | 2/2015 | Kreuzer ................ A61F 13/533 604/372 |
| 2015/0065975 A1 | 3/2015 | Roe et al. |
| 2015/0065981 A1 | 3/2015 | Roe et al. |
| 2015/0065986 A1 | 3/2015 | Blessing et al. |
| 2015/0080821 A1 | 3/2015 | Peri et al. |
| 2015/0080837 A1 | 3/2015 | Rosati et al. |
| 2015/0080839 A1 | 3/2015 | Trapp et al. |
| 2015/0173967 A1 | 6/2015 | Kreuzer et al. |
| 2015/0173968 A1 | 6/2015 | Joseph |
| 2015/0250662 A1 | 9/2015 | Isele et al. |
| 2015/0250663 A1 | 9/2015 | Wagner et al. |
| 2015/0273433 A1 | 10/2015 | Nakatsuru et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0700673 | 3/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |

(56) References Cited

FOREIGN PATENT DOCUMENTS

| | | |
|---|---|---|
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0988846 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 752892 | 7/2001 |
| EP | 1116479 A2 | 7/2001 |
| EP | 0790839 | 8/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2656826 | 10/2013 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | H10295728 | 11/1998 |
| JP | 10328232 | 12/1998 |
| JP | 11033056 A | 2/1999 |
| JP | 11318980 | 11/1999 |
| JP | 11320742 | 11/1999 |
| JP | 2000232985 | 8/2000 |
| JP | 2000238161 | 9/2000 |
| JP | 2001037810 | 2/2001 |
| JP | 2001046435 A | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 2001258935 | 9/2001 |
| JP | 2001277394 | 10/2001 |
| JP | 2001301857 | 10/2001 |
| JP | 03420481 B2 | 11/2001 |
| JP | 2001321397 | 11/2001 |
| JP | 2001353174 A | 12/2001 |
| JP | 2002052042 A | 2/2002 |

(56) References Cited

FOREIGN PATENT DOCUMENTS

| | | |
|---|---|---|
| JP | 2002065718 | 3/2002 |
| JP | 2002113800 A | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002320641 | 11/2002 |
| JP | 2002325792 A | 11/2002 |
| JP | 2002325799 A | 11/2002 |
| JP | 2002369841 A | 12/2002 |
| JP | 2003126140 | 5/2003 |
| JP | 2003153955 A | 5/2003 |
| JP | 2003265523 | 9/2003 |
| JP | 2003265524 A | 9/2003 |
| JP | 2003275237 | 9/2003 |
| JP | 2003325563 | 11/2003 |
| JP | 2004089269 | 3/2004 |
| JP | 03566012 B2 | 6/2004 |
| JP | 03568146 B2 | 6/2004 |
| JP | 2004222868 | 8/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 2005118339 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007130504 | 5/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 4177770 B2 | 11/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009028186 | 2/2009 |
| JP | 2009082481 | 4/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010046155 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010194218 | 9/2010 |
| JP | 2010201093 | 9/2010 |
| JP | 2010221067 | 10/2010 |
| JP | 4577766 B2 | 11/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |

(56) References Cited

FOREIGN PATENT DOCUMENTS

| | | |
|---|---|---|
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 2011240050 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 2012100886 | 5/2012 |
| JP | 05016020 B2 | 6/2012 |
| JP | 05027364 B2 | 6/2012 |
| JP | 2012115378 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125452 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 2012179286 | 9/2012 |
| JP | 05113146 B2 | 10/2012 |
| JP | 05129536 B2 | 11/2012 |
| JP | 2012223230 | 11/2012 |
| JP | 2012223231 | 11/2012 |
| JP | 05105884 B2 | 12/2012 |
| JP | 5291238 | 9/2013 |
| JP | 5715806 B2 | 5/2015 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO96029967 | 10/1996 |
| WO | WO9711659 | 4/1997 |
| WO | WO9717922 | 5/1997 |
| WO | WO 9724096 | 7/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO 99/51178 | 10/1999 |
| WO | WO200000235 | 1/2000 |
| WO | WO200032145 | 6/2000 |
| WO | WO200059430 | 10/2000 |
| WO | WO200115647 | 3/2001 |
| WO | WO200126596 | 4/2001 |
| WO | WO 0135886 | 5/2001 |
| WO | WO200207663 | 1/2002 |
| WO | WO200232962 | 4/2002 |
| WO | WO2002064877 | 8/2002 |
| WO | WO2002067809 | 9/2002 |
| WO | WO2003009794 | 2/2003 |
| WO | WO2003039402 | 5/2003 |
| WO | WO2003053297 | 7/2003 |
| WO | WO03079946 | 10/2003 |
| WO | WO03101622 | 12/2003 |
| WO | WO2003105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO 2005/102237 | 11/2005 |
| WO | WO2006104024 | 5/2006 |
| WO | WO2006059922 | 6/2006 |
| WO | WO2006062258 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO 2007/141744 | 12/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005114 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |

(56) References Cited

FOREIGN PATENT DOCUMENTS

| WO | WO2012073499 | 6/2012 |
|----|--------------|--------|
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117764 | 9/2012 |
| WO | WO2012117824 | 9/2012 |
| WO | WO2012132460 | 10/2012 |
| WO | WO 2012/177400 | 12/2012 |
| WO | WO2012170778 | 12/2012 |
| WO | WO2012170779 | 12/2012 |
| WO | WO2012170781 | 12/2012 |
| WO | WO2012170783 | 12/2012 |
| WO | WO2012170808 | 12/2012 |
| WO | WO2012174026 | 12/2012 |
| WO | WO2013001788 | 1/2013 |
| WO | WO2013021651 | 2/2013 |
| WO | WO2013046701 | 4/2013 |
| WO | WO2013056978 | 4/2013 |
| WO | WO2013060733 | 5/2013 |
| WO | WO2013077074 | 5/2013 |
| WO | WO2014073636 | 5/2014 |
| WO | WO2014078247 | 5/2014 |
| WO | WO2014093310 | 6/2014 |
| WO | WO2015095514 | 6/2015 |
| WO | WO2016040091 | 3/2016 |

\* cited by examiner

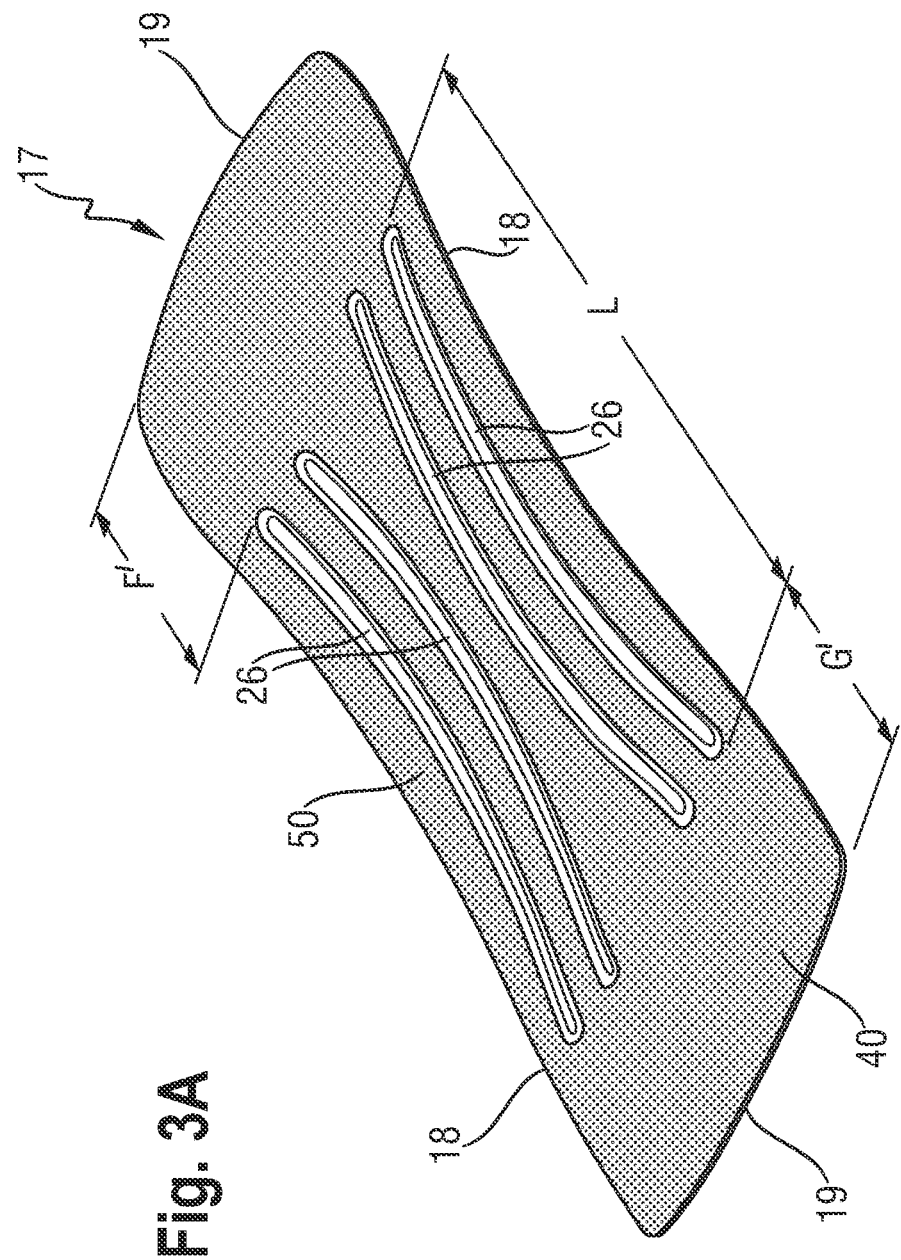

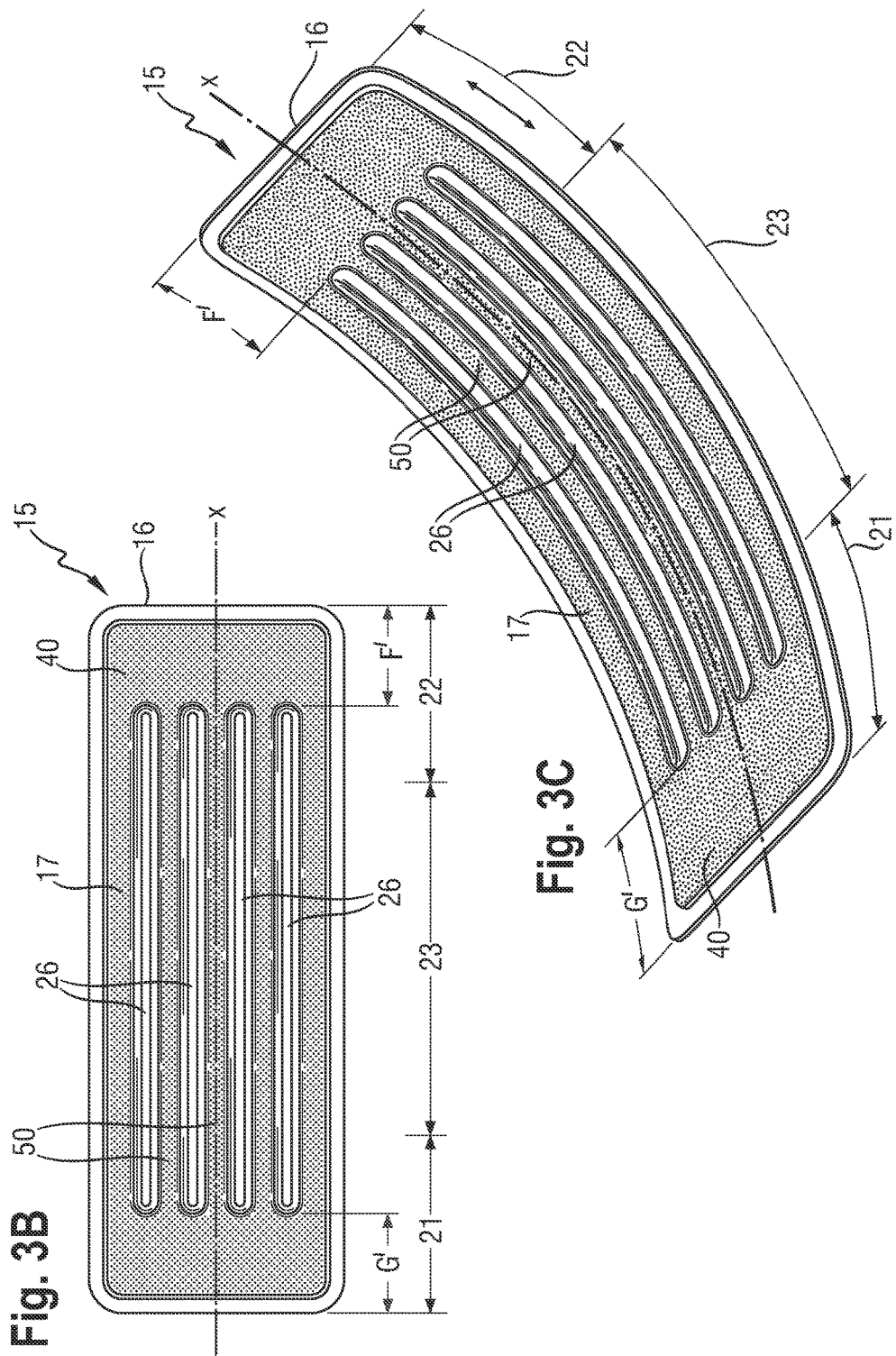

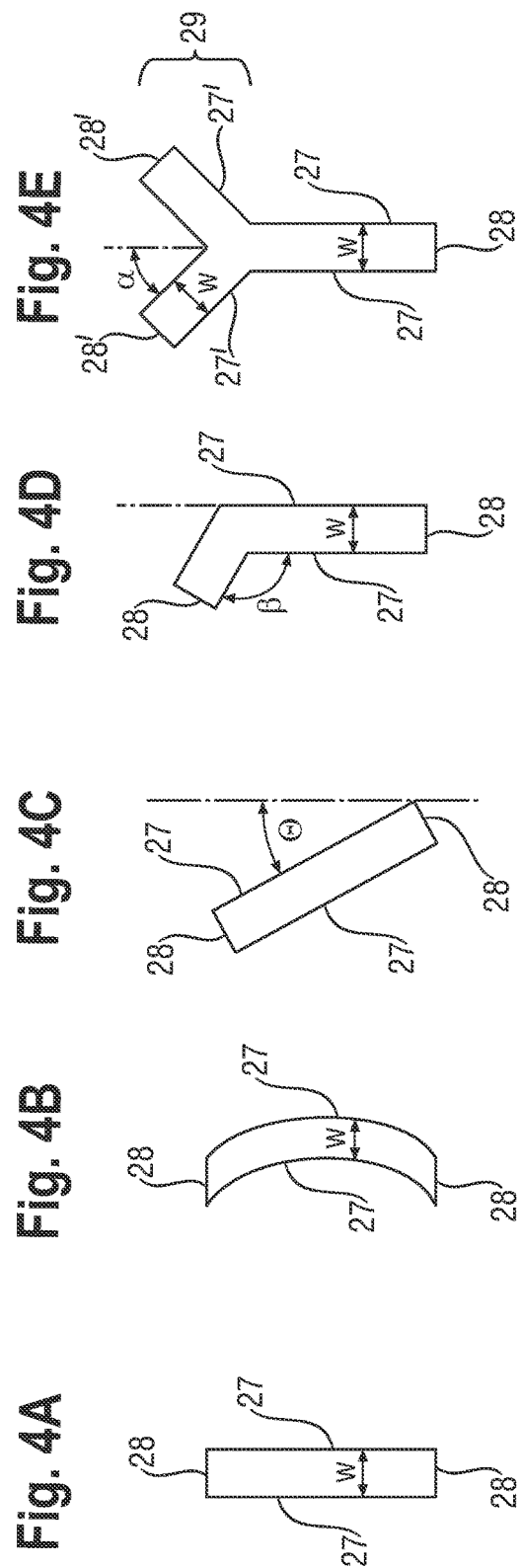

ically known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

DISPOSABLE DIAPERS

CROSS REFERENCE TO RELATED APPLICATION

This application claims the benefit of U.S. Provisional Patent Application Ser. No. 61/495,406, filed Jun. 10, 2011, which is hereby incorporated by reference in its entirety.

FIELD

The present disclosure relates to disposable diapers providing an improved fit in dry and wet states (i.e., when loaded with bodily fluids) and providing improved liquid transportation.

BACKGROUND

Disposable absorbent articles for receiving and retaining bodily discharges such as urine or feces are generally known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

Since their introduction into the market place, disposable diapers have continued to improve regarding comfort, fit and functionalities.

An important component of disposable absorbent articles is the absorbent core structure. The absorbent core structure typically includes absorbent polymer material, such as hydrogel-forming polymer material, also referred to as absorbent gelling material, AGM, or super-absorbent polymer, SAP. This absorbent polymer material ensures that large amounts of bodily fluids, e.g. urine, can be absorbed by the absorbent article during its use and be locked away, thus providing low rewet and good skin dryness.

Traditionally, the absorbent polymer material is incorporated into the absorbent core structure with cellulose or cellulosic fibres. However, over the past years, significant effort has been spent to make thinner absorbent core structures which can still acquire and store large quantities of discharged body fluids, in particular urine. Hereto, it has been proposed to reduce or eliminate these cellulose fibres from the absorbent core structures. To maintain the mechanical stability of the absorbent core structures, small quantities of thermoplastic adhesive material, such as fibrous thermoplastic adhesive material, may be added to stabilize the absorbent polymer material. Resultantly, absorbent structures having the required permeability/porosity, reduced gel-blocking, and that form stable structures in use or transport are provided.

However, it was found that some absorbent core structures with reduced cellulose fibre content, whilst being very thin when not loaded with bodily fluids, may have an increased stiffness when partially loaded or fully loaded, especially in those regions which comprise most of the absorbent capacity of the absorbent article, such as the front region and crotch region of the diaper. Increased stiffness is not desirable since it reduces the absorbent article's ability to conform to the body of the wearer once worn. Furthermore, it was also found that some absorbent core structures which comprise absorbent polymer particles of high absorption capacity swell significantly upon loading with body exudates. As a result, the volume of the absorbent article may increase significantly during use, especially in these regions which comprise most of the absorbent capacity of the absorbent article, such as the front region and crotch region of the diaper. Such an increase in volume may render the disposable article uncomfortable for the wearer. It was also found that some of these absorbent core structures with reduced cellulose fibres content may have a reduced void volume which impacts negatively the liquid acquisition speed.

Therefore there is still a need for disposable diapers having good liquid handling properties and having an increased flexibility during the whole use of the article and which deliver, in particular, a better fit in the wet state.

SUMMARY

The present disclosure generally relates to a disposable diaper having a transverse and longitudinal dimension. The disposable diaper comprises a backsheet, a topsheet and an absorbent core disposed therebetween. The absorbent core comprises at least one absorbent structure comprising a substrate layer and an absorbent layer. The absorbent layer comprises absorbent polymer particles, and optionally cellulose fibers, supported by and immobilized on the substrate layer. The absorbent layer has a transverse and longitudinal dimension and a thickness, a pair of opposing longitudinal edges extending in the longitudinal dimension, a pair of opposing transversal edges extending in its transverse dimension and a front, crotch and back regions arranged sequentially in the longitudinal dimension. A plane having a dimension that is coextensive with the central longitudinal axis of the absorbent layer and another dimension extending in a direction perpendicular to both the longitundinal and transverse directions delimits two longitudinal portions. The absorbent layer comprises at least two channels substantially free of said absorbent polymer particles extending through its thickness in its longitudinal dimension, each longitudinal portion of the absorbent layer comprising one of said channels. Each channel has a width of at least 3 mm or of at least 4% of the transverse dimension of the absorbent layer, extends over at least 15% of the longitudinal dimension of the absorbent layer and is at least present in the crotch region or part thereof. The absorbent layer may not comprise channels substantially free of absorbent polymer particles extending in its transverse dimension in the crotch region and may not comprise channels substantially free of absorbent polymer particles extending up to its longitudinal and transverse edges.

BRIEF DESCRIPTION OF THE DRAWINGS

FIG. 3A is a perspective view of an absorbent layer comprising four longitudinal main channels in accordance with one non-limiting embodiment.

FIG. 3B is a top view of an absorbent structure comprising an absorbent layer with four longitudinal main channels in accordance with one non-limiting embodiment.

FIG. 3C is a perspective view of the absorbent structure of FIG. 3B in accordance with one non-limiting embodiment.

FIGS. 4A to 4E are schematic representations of channels in accordance with various non-limiting embodiments.

DETAILED DESCRIPTION

Definitions

Figure 1:
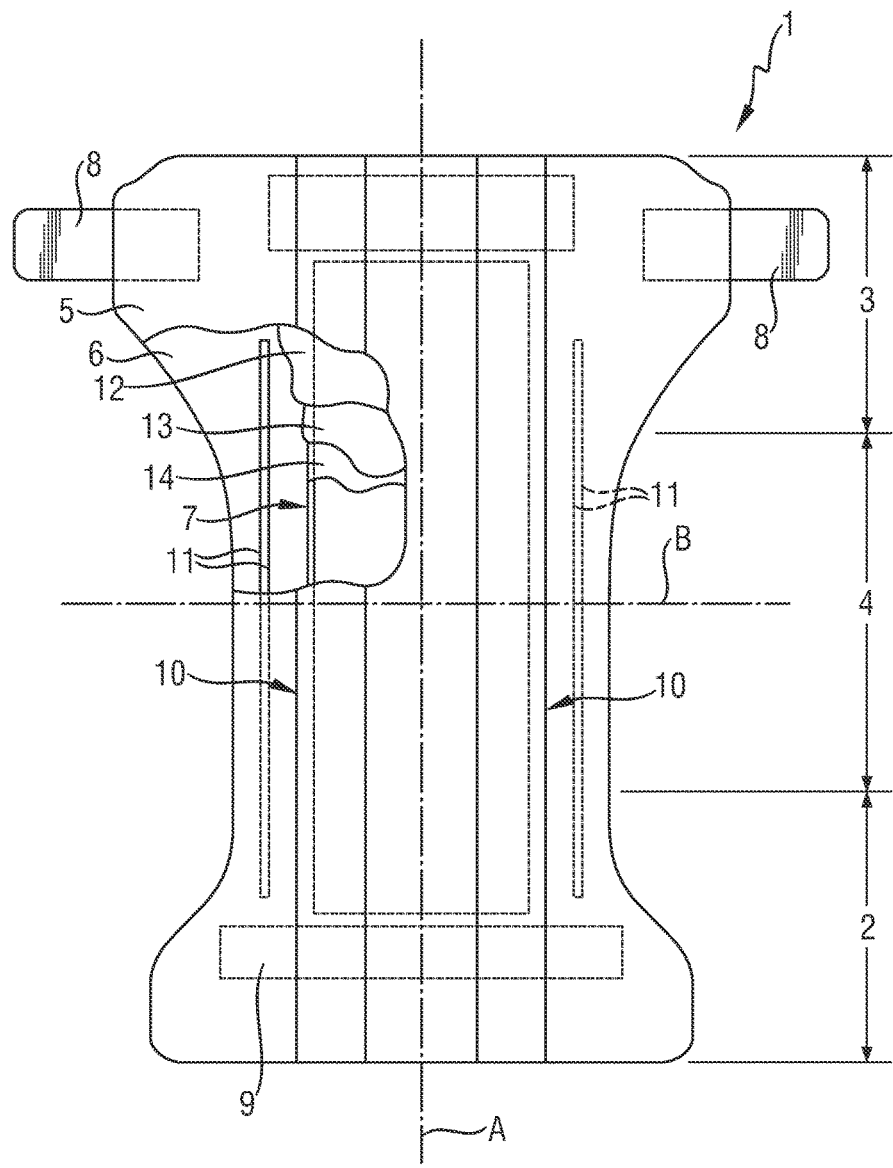
FIG. 1 is a plan view of a disposable diaper in accordance with one non-limiting embodiment.

As used herein "diapers" refers to devices which are intended to be placed against the skin of a wearer to absorb and contain the various exudates discharged from the body. Diapers are generally worn by infants and incontinent persons about the lower torso so as to encircle the waist and legs of the wearer. Examples of diapers include infant or adult diapers and pant-like diapers such as training pants.

"Training pant", as used herein, refers to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Disposable" is used herein to describe articles that are generally not intended to be laundered or otherwise restored or reused (i.e., they are intended to be discarded after a single use and, may be recycled, composted or otherwise disposed of in an environmentally compatible manner).

As used herein "absorbent structure" refers to a three dimensional structure useful to absorb and contain liquids, such as urine. The absorbent structure may be the absorbent core of an absorbent article or may be part of the absorbent core of an absorbent article, i.e. an absorbent component of the absorbent core, as will be further described herein.

As used herein "absorbent core" refers to a component of an absorbent article typically disposed between a topsheet and backsheet of an absorbent article. The absorbent core of an absorbent article may comprise one or more absorbent structures and optionally further layers, such as for instance a cover layer.

"Absorbent polymer particles" as used herein refers to substantially water-insoluble polymer particles that can absorb at least 10 times their weight of a 0.9% saline solution in de-mineralized water as measured using the Centrifuge Retention Capacity test (Edana 441.2-01).

"Nonwoven material" as used herein refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which may comprise spunlaying, meltblowing, carding, airlaying, wetlaying, coform and combinations thereof. The fibers may be of natural or man-made origin and may be staple fibers or continuous filaments or be formed in situ.

The term "basis weight" as used herein refers to the mass of a material per unit area, i.e. the mass of absorbent polymer particles per unit area, e.g. gram per square meter (gsm).

"Hot melt adhesive" as used herein refers to adhesives in alignment with the description given in "Adhesion and Adhesives Technology: An Introduction" by Alphonsus V. Pocius (Hanser publishers Munich, 1997). Therein a hot melt is defined as an adhesive applied from the melt and gaining strength upon solidification.

In the following description of the present disclosure, the surface of the disposable diaper, or of an element thereof, which faces in use in the direction of the wearer, is called the "wearer-facing surface". Conversely, the surface facing in use in the direction of the garment is called the "garment-facing surface". The disposable diaper, as well as any element thereof, such as, for example the absorbent structure, has therefore a wearer-facing surface and a garment-facing surface.

Unless specified otherwise, the longitudinal dimension or length of an absorbent layer as used herein is to be understood as the average length.

Unless specified otherwise, the transverse dimension or width of an absorbent layer as used herein is to be understood as the average width.

Disposable Diapers

The disposable diaper 1, such as illustrated in FIG. 1, has a longitudinal dimension (along a longitudinal axis A) and a transverse dimension (along a transverse axis B) perpendicular thereto.

One end portion of the diaper is configured as a front waist region 2 (which is the front one third of the article, having one third of the length of the article). The opposite end portion is configured as a back waist region 3 (which is the back one third of the article, having one third of the length of the article). An intermediate portion of the diaper is configured as a crotch region 4 (which is the centre one third of the article). The crotch region extends longitudinally between the front and back waist regions. The crotch region is that portion of the diaper which, when the diaper is worn, is generally positioned between the wearer's legs.

The diaper typically comprises a topsheet 5, a backsheet 6 and an absorbent core 7 disposed therebetween.

The topsheet may be liquid pervious. The topsheet may be at least partially hydrophilic. So-called apertured topsheets may also be used. Topsheets with one or more (large) openings may also be used. The topsheet may also include a skin care composition, e.g., a lotion. The topsheet may be fully or partially elasticized or may be foreshortened to provide a void space between the topsheet and the absorbent core. Example structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet may be vapor pervious but liquid impervious. The backsheet may be used to at least inhibit the fluids absorbed and contained in the absorbent core from wetting materials that contact the absorbent article such as underpants, pants, pyjamas, undergarments, and shirts or jackets, thereby acting as a barrier to fluid transport. In certain embodiments, the backsheet may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964.Other suitable backsheet materials may include breathable materials that permit vapors to escape from the diaper while still at least inhibiting liquid exudates from passing through the backsheet. Example breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

The absorbent core 7 is disposed between the topsheet and the backsheet of the absorbent article. The absorbent core may comprise one or more absorbent structures as disclosed herein.

The diaper may further comprise a front and back waist band and/ or a fastening system, typically joined to the waistband, as known in the art. Desired fastening systems comprise fastening tabs 8 and landing zones 9, wherein the fastening tabs are attached or joined to the back waist region of the diaper and the landing zones are part of the front waist region of the diaper. The diaper may also have leg cuffs 10 and/or barrier cuffs, such as elasticized barrier cuffs 11. Suitable cuffs are described, for example, in U.S. Pat. Nos. 3,860,003; 4,808,178 and 4,909; U.S. Pat. Nos. 4,695,278 and 4,795,454.

As illustrated in FIG. 1, the absorbent core may comprise an acquisition system comprising an upper acquisition layer 12 and a lower acquisition layer 13 and optionally a core cover 14.

Processes for assembling the diaper include conventional techniques generally known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. While the topsheet, the backsheet, and the absorbent core may be assembled in a variety of well-known configurations, desired diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

As indicated above, the absorbent core may comprise one or more absorbent structures that absorb and contain liquids, such as urine. The absorbent structure may be the absorbent core of an absorbent article or may be part of the absorbent core of an absorbent article.

Absorbent Structure

Figure 2:
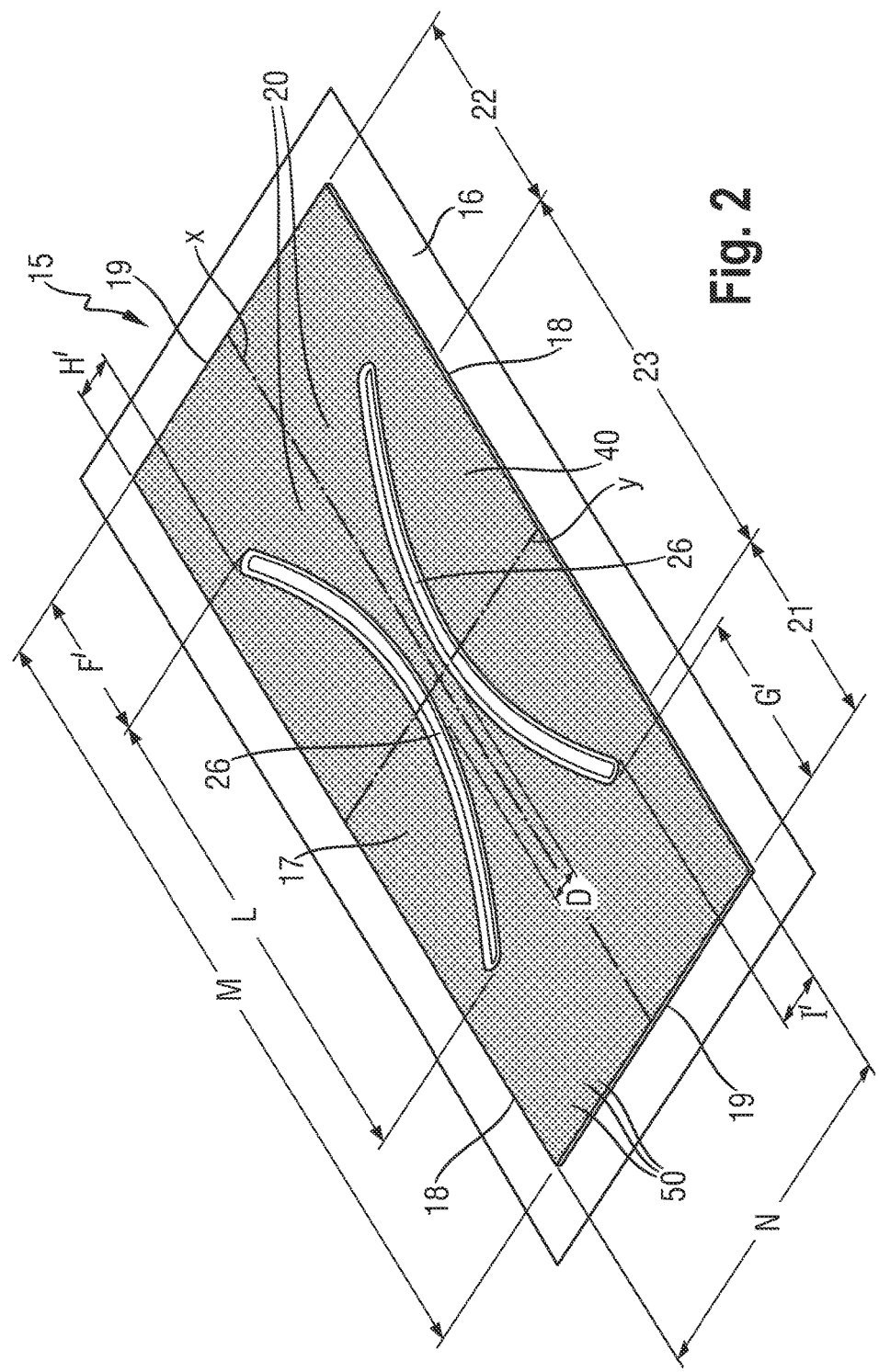
FIG. 2 is a perspective view of an absorbent structure comprising an absorbent layer with two longitudinal main channels in accordance with one non-limiting embodiment.

The absorbent structure 15 is a three-dimensional structure comprising a substrate layer 16 and an absorbent layer 17 comprising absorbent polymer particles, and optionally cellulose, supported by, and immobilized on, said substrate layer 16. Examples of absorbent structures 15 are illustrated in FIGS. 2, 3B and 3C.

Figure 5:
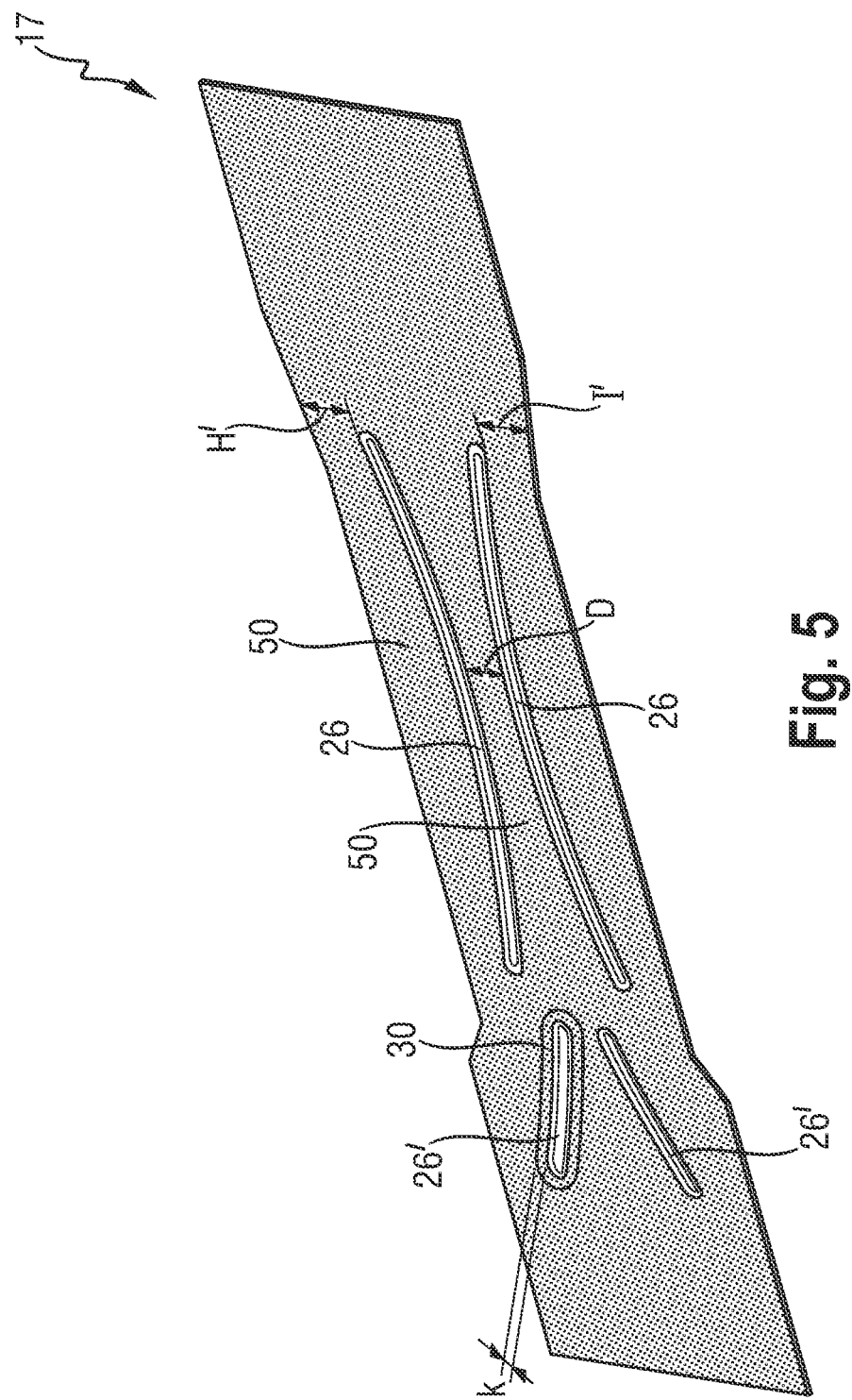
FIG. 5 is a perspective view of an absorbent layer comprising two longitudinal main channels at least present in the crotch region and two longitudinal secondary channels in the front region in accordance with one non-limiting embodiment.
Figure 6:
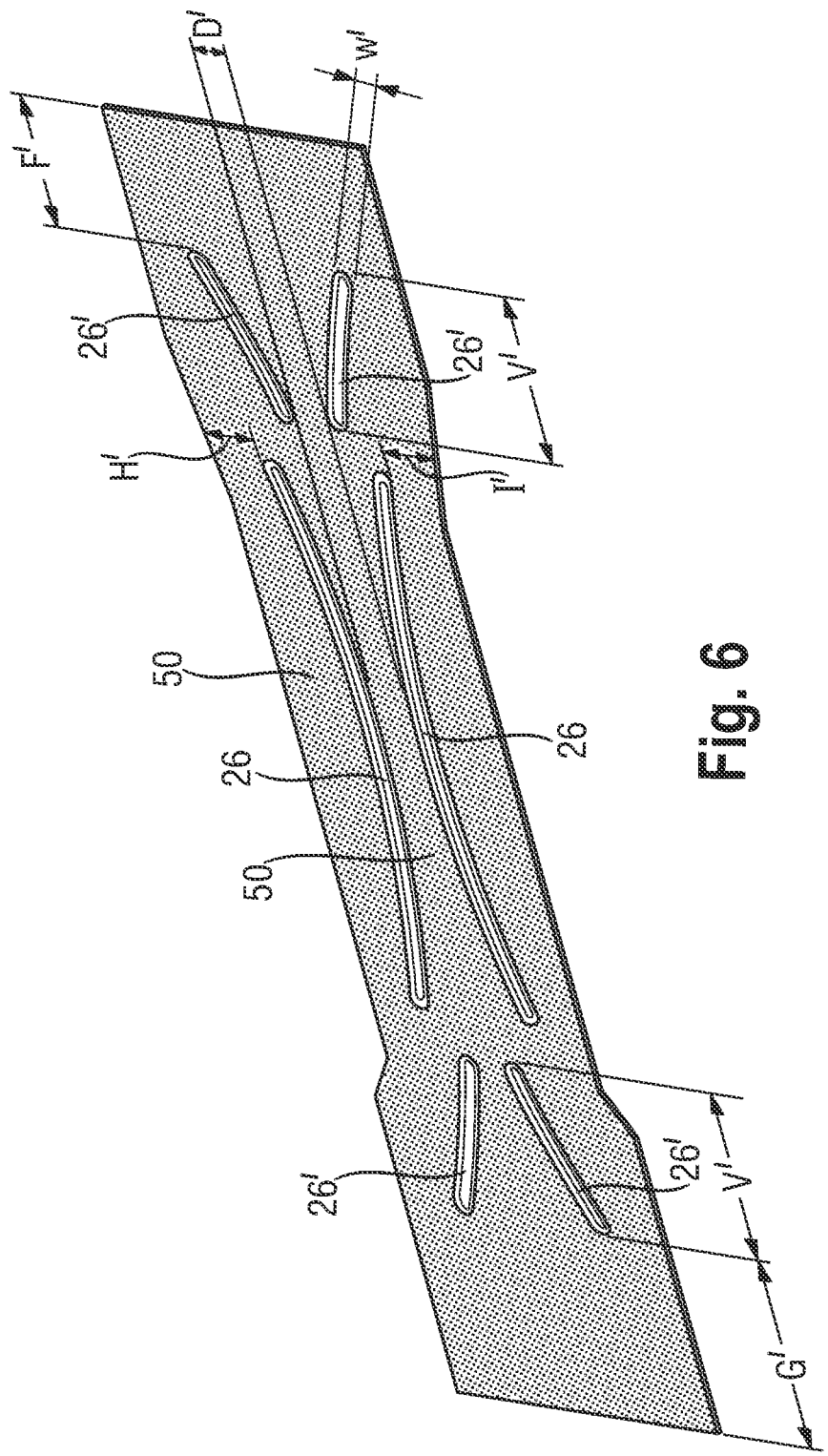
FIG. 6 is a perspective view of an absorbent layer comprising two longitudinal main channels at least present in the crotch region, two longitudinal secondary channels in the front region and two longitudinal secondary channels in back front region in accordance with one non-limiting embodiment.

The substrate layer has a longitudinal dimension extending in the longitudinal dimension of the diaper and a transverse dimension extending in the transverse dimension of the diaper The absorbent layer has a longitudinal dimension M extending in the longitudinal dimension of the diaper (i.e. the absorbent layer has a length M) and a transverse dimension N extending in the transverse dimension of the diaper (i.e. the absorbent layer has a width N). The absorbent layer possesses a central longitudinal axis x, a central transverse axis y perpendicular to said central longitudinal axis x, a pair of opposing longitudinal edges 18 extending in the longitudinal dimension of the disposable diaper and a pair of opposing transverse edges 19 extending in the transverse dimension of the disposable diaper. The longitudinal edges or transverse edges of the absorbent layer may be parallel respectively to the central longitudinal axis or central transverse axis (as shown in FIG. 2) or they may follow the general direction of these axes while not being strictly parallel, e.g. they may be curvilinear as for instance to provide for a narrower transverse dimension in the crotch region (as shown in FIG. 3A, 5 and 6).

The central longitudinal axis x of the absorbent layer 17 delimits two regions of the absorbent layer referred herein as longitudinal regions 20 (the plane having a dimension coextensive with the central longitudinal axis and another dimension perpendicular to both the longitudinal and transverse axes divides the absorbent layer 17 in two longitudinal regions 20 disposed on either side of said plane).

One end portion of the absorbent layer is configured as a front region 21 (which is the region oriented toward the front waist region of the disposable diaper) which makes up 25% of the longitudinal dimension M of the absorbent layer 17. The opposite end region is configured as a back region 22 (which is the region oriented toward the back waist region of the diaper) which makes up 25% of the longitudinal dimension M of the absorbent layer 17. An intermediate portion of the absorbent layer 17 is configured as a crotch region 23 which makes up 50% of the longitudinal dimension M of the absorbent layer. The front, crotch and back regions are arranged sequentially in the longitudinal dimension of the absorbent layer.

The substrate layer of the absorbent structure may be any material capable to support the absorbent polymer particles. Typically, it is a web or sheet material, such as foam, film woven and/or nonwoven material. "Nonwoven material" as used herein refers to a manufactured web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. Nonwoven materials and processes for making them are generally known in the art. Generally, processes for making nonwoven materials comprise two steps: fiber laying onto a forming surface and fiber bonding. The fiber laying step may comprise spunlaying, meltblowing, carding, airlaying, wetlaying, coform and combinations thereof. The fiber bonding step may comprise hydroentanglement, cold calendering, hot calendering, through air thermal bonding, chemical bonding, needle punching, and combinations thereof. The nonwoven material may be a laminate. The laminate may comprise spunbond layer(s) (S), and/or meltblown layer(s) (M), and/or carded layer(s) (C). Suitable laminates include, but are not limited to, SS, SSS, SMS or SMMS. The nonwoven material may have a basis weight from about 5 to 100 g/m², or from about 10 to 40 g/m², or from about 10 to 30 g/m². Woven or nonwoven materials may comprise natural fibers or synthetic fibers or combinations thereof. Examples of natural fibers may include cellulosic natural fibers, such as fibers from hardwood sources, softwood sources, or other non-wood plants. The natural fibers may comprise cellulose, starch and combinations thereof. The synthetic fibers can be any material, such as, but not limited to, those selected from the group consisting of polyolefins (polypropylene and polypropylene copolymers), polyethylene and polyethylene copolymers), polyesters (e.g., polyethylene terephthalate), polyethers, polyamides, polyesteramides, polyvinylalcohols, polyhydroxyalkanoates, polysaccharides, and combinations thereof. Further, the synthetic fibers can be a single component (i.e. a single synthetic material or a mixture that makes up the entire fiber), bi-component (i.e. the fiber is divided into regions, the regions including two or more different synthetic materials or mixtures thereof and may include co-extruded fibers and core and sheath fibers) and combinations thereof. Bi-component fibers can be used as a component fiber of the nonwoven material, and/or they may be present to act as a binder for the other fibers present in the nonwoven material. Any or all of the fibers may be treated before, during, or after manufacture to change any desired properties of the fibers.

The substrate layer 16 and the absorbent layer 17 may be coextensive or the substrate layer 16 may be slightly longer and wider than the absorbent layer 17 (as shown in FIGS. 2, 3B and 3C).

The absorbent layer 17 comprises absorbent polymer particles 50, and optionally cellulose. Absorbent polymer particles will be described in further details herein below. The absorbent polymer particles may be used alone or in combination with other materials. In some embodiments, the absorbent layer comprises absorbent polymer particles combined with cellulose. "Cellulose" as used herein refers to comminuted wood pulp in the form of fibers, typically also referred in the art as "air-felt". In some embodiments, the absorbent layer comprises more than 70%, or more than 80%, or more than 90%, or more than 95% or even 100% by weight of absorbent polymer particles. In some other embodiments, the absorbent layer comprises absorbent polymer particles and less than 5% by weight of cellulose, more typically less than 2% by weight of cellulose and most typically the absorbent layer is cellulose free. In embodiments wherein the absorbent layer is cellulose free, the absorbent layer comprises only absorbent polymer particles. The resulting absorbent structures have a reduced thickness in the dry state compared to conventional absorbent structure comprising cellulosic fibers. The reduced thickness helps to improve the fit and comfort of the absorbent article for the wearer.

The absorbent layer 17 comprises at least two channels 26 substantially free of absorbent polymer particles extending through the thickness of the absorbent layer in the longitudinal dimension of the absorbent layer. By extending in the longitudinal dimension of the absorbent layer, it is meant that the channels extend essentially in the longitudinal dimension, i.e. they extend more in the longitudinal dimension than in the transverse dimension, e.g. at least twice as much in the longitudinal dimension than in the transverse dimension. These two channels are referred herein as "longitudinal main channels".

In addition to these two longitudinal main channels 26, the absorbent layer 17 may comprise further channels 26', referred herein as "secondary channels".

"Channels" as used herein refer to discrete portions of the absorbent layer extending through the thickness of the absorbent layer which are substantially free of absorbent polymer particles, i.e. no absorbent polymer particles are intentionally present in such a channel (longitudinal main channel or secondary channel) of an absorbent structure. However, it should be understood that, accidentally, a small, negligible amount of absorbent polymer particles may be present in the channel, which may not contribute to the overall functionality (e.g. absorbency of the absorbent structure). Typically, the channels possess two transverse edges (in the shortest dimension) and two longitudinal edges (in the longest dimension) running between the transverse edges. The transverse edges of the channels may be straight (i.e. perpendicular to the longitudinal side edges), angled or curved. The channels have an average width w of at least 3 mm (the average of a channel is defined as the average distance between the longitudinal side edges) or of at least 4% of the width of the absorbent layer. In some embodiments, the longitudinal channels may have complex shapes: the channels may not end with a straight, angled or curved traverse edge but may have one or more ramifications at one or the two of their end edges (referred herein as ramified channels). The ramifications also possess longitudinal edges and one transverse edge. The channels, as well as their ramifications, have an average width w of at least 3 mm or of at least 4% of the width of the absorbent layer.

The channels may be permanent. By permanent, it is meant that the integrity of the channels is at least partially maintained both in dry state and wet state, i.e. the channels are resistant to frictions caused by movements of the diaper's wearer and resist wetting by bodily fluids, such as urine. Permanent channels are obtained by immobilizing the absorbent polymer particles on the substrate layer, such as by applying a thermoplastic adhesive material over the absorbent layer. Alternatively, the channels may be made permanent by folding the substrate layer into the channels or allowing the substrate layer to enter the channels so as to immobilize the absorbent polymer particles as will be described in further details herein below.

The absorbent cores (7) of the present disclosure may comprise in particular permanent channels formed by bonding of the first substrate layer (16) and second substrate layer (16') through the channels. Typically, glue may be used to bond both substrate layers through the channel, but it is possible to bond via other known means, for example ultrasonic bonding, or heat bonding. The supporting layers can be continuously bonded or intermittently bonded along the channels.

The Wet Channel Integrity Test described below can be used to test if channels are permanent following wet saturation and to what extent.

Wet Channel Integrity Test

This test is designed to check the integrity of a channel following wet saturation. The test can be performed directly on an absorbent structure or on an absorbent core containing the absorbent structure.

1. The length (in millimeters) of the channel is measured in the dry state (if the channel is not straight, the curvilinear length through the middle of the channel is measured).
2. The absorbent structure or core is then immersed in 5 liters of synthetic urine "Saline", with a concentration of 9.00 g NaCl per 1000 ml solution prepared by dissolving the appropriate amount of sodium chloride in distilled water. The temperature of the solution must be 20 +/−5° C.
3. After 1 minute in the saline, the absorbent structure or core is removed and held vertically by one end for 5 seconds to drain, then extended flat on a horizontal surface with the garment-facing side down, if this side is recognizable. If the absorbent structure or core comprises stretch elements, the absorbent structure or core is pulled taut in both X and Y dimensions so that no contraction is observed. The extremes/edges of the absorbent structure or core are fixed to the horizontal surface, so that no contraction can happen.
4. The absorbent structure or core is covered with a suitably weighted rigid plate, with dimensions as follows: length equal to the extended length of the absorbent structure or core, and width equal to the maximum absorbent structure or core width in the cross direction.
5. A pressure of 18.0 kPa is applied for 30 seconds over the area of the rigid plate above mentioned. Pressure is calculated on the basis of overall area encompassed by the rigid plate. Pressure is achieved by placing additional weights in the geometric center of the rigid plate, such that the combined weight of the rigid plate and the additional weights result in a pressure of 18.0 kPa over the total area of the rigid plate.
6. After 30 seconds, the additional weights and the rigid plate are removed.
7. Immediately afterwards, the cumulative length of the portions of the channel which remained intact is measured (in millimeters; if the channel is not straight, the curvilinear length through the middle of the channel is measured). If no portions of the channel remained intact then the channel is not permanent.
8. The percentage of integrity of the permanent channel is calculated by dividing the cumulative length of the portions of the channel which remained intact by the length of the channel in the dry state, and then multiplying the quotient by 100.

Advantageously, a permanent channel according to the present disclosure has a percentage of integrity of at least 20%, or 30%, or 40%, or 50%, or 60, or 70%, or 80%, or 90% following this test.

When the absorbent structure comprises absorbent polymer particles and cellulose, it may be desired that said channels, i.e. longitudinal main channels and/or secondary channels, are also free of such cellulose.

In the following, when applicable, the description applies to each channel taken independently. For example, by "two longitudinal channels may extend over a distance L which is at least 15%", it is meant that each of the two longitudinal channels may extend over a distance L which is at least 15% . . . ", i.e. the channels may be the same or different.

Longitudinal Main Channels

The two longitudinal main channels 26 may be distributed in the absorbent layer 17 such that each longitudinal portion 20 of the absorbent layer comprises one longitudinal main channel 26.

As shown in FIG. 2, the two longitudinal main channels are at least present in the crotch region of the absorbent layer. By "at least present in the crotch region", it is meant that the channels may be only present in the crotch region or they may extend from the crotch region up to the front region and/or up to the back region, i.e. they may extend beyond the crotch region. In some embodiments, the two longitudinal main channels may extend across at least 15%, or at least 20% or at least 30% and up to 50%, or up to 70% or up 90% of the longitudinal dimension of the absorbent layer (i.e. they may extend over a distance L which is at least 15% and up to 50%, or up to 70% or up 90% of the length M of the absorbent layer). In some embodiments, the two longitudinal main channels may be present only in the crotch region. When present only in the crotch region, the longitudinal main channels may extend over the whole longitudinal dimension of the crotch region, i.e. 50% of the longitudinal dimension M of the absorbent layer, or they may extend in only part of the crotch region, i.e. from at least 15%, or at least 20% or at least 30% to 40%, or to 45% or to less than 50% of the longitudinal dimension of the absorbent layer. In some embodiments, the two longitudinal main channels 26 may be present in the crotch region, or part thereof, and part of the front region and/or part of the back region (such as shown in FIG. 2). In some embodiments, the longitudinal main channels may be present in the front and crotch regions, i.e. the channels extend through the crotch region (or part thereof) and part of the front region. In these embodiments, the longitudinal main channels may extend up to 70% of the longitudinal dimension of the absorbent layer, typically from 15%, or from 30%, or from 35% or from 40% to 70% of the longitudinal dimension of the absorbent layer (i.e. they may extend over a distance L which is up to 70% of the length M of the absorbent layer). In some embodiments, the longitudinal main channels may be present in the back and crotch regions, i.e. the channels extend through the crotch region (or part thereof) and part of the back region. In these embodiments, the longitudinal main channels may extend up to 70% of the longitudinal dimension of the absorbent layer, typically from 15%, or from 30%, or from 35% or from 40% to 70% of the longitudinal dimension of the absorbent layer (i.e. they may extend over a distance L which is up to 70% of the length M of the absorbent layer). In some embodiments, the longitudinal main channels may be present in the front, crotch and back regions. In these embodiments, the longitudinal main channels may extend up to 90% of the longitudinal dimension M of the absorbent layer, typically from 55% or from 60% to 70%, or to 80% of the longitudinal dimension of the absorbent layer (i.e. they may extend over a distance L which is up to 90% of the length M of the absorbent layer).

The longitudinal main channels 26 may be mirror images of one another with respect to the central longitudinal axis x of the absorbent layer 17, i.e. the longitudinal main channel in one longitudinal region 20 may be mirror image of the longitudinal main channel in the other longitudinal region of the absorbent layer 17.

The longitudinal main channels 26 may not extend up to the transverse edges 19 of the absorbent layer 17, i.e. from one transverse edge to the other. Typically, the absorbent layer comprises, along each transverse edge and immediately adjacent to said edge, a strip free of channels which extends in the transverse dimension of the absorbent layer from one longitudinal edge to the other. Said strips have respectively a width F' or G' which is at least 5% of the longitudinal dimension of the absorbent layer (i.e. a width which is at least 5% of the length of the absorbent layer). In other words, the smallest distance F' or G' between the edge of a channel and the transverse edge of the absorbent layer is at least 5% of the longitudinal dimension M of the absorbent layer. In some embodiments, the width F' or G' is at least from 5% to 15%, or to 10% of the longitudinal dimension of the absorbent layer.

Furthermore, in order to reduce the risk of fluid leakages and run-off, the longitudinal main channels may not extend up to the longitudinal edges 18 of the absorbent layer 17. Typically, the absorbent layer comprises, along each longitudinal edge and immediately adjacent to said edge, a strip free of channel which extends in the longitudinal dimension of the absorbent layer from one transverse edge to the other. Said strips have respectively a width I' or F' which is at least 5%, or at least 10%, or at least 12% to 25% of the transverse dimension N of the absorbent layer in a given region (i.e. a width I' or F' which is at least 5% of the width N of the absorbent layer). In other words, the minimum distance I' or F' between the edge of a channel and the longitudinal edge of the absorbent layer is at least from 5% to 25% of the transverse dimension of the absorbent layer. For example, the distance I' or F' in the crotch region may correspond to at least 5%, or to at least 10% or at least 12% of the transverse dimension N of the absorbent layer in said crotch region. In some embodiments, the distance I' and/or F' is of 10 mm, or 15 mm or 20 mm.

The longitudinal main channels may be straight channels running parallel to the longitudinal axis of the absorbent layer (as shown schematically in FIG. 4A). Straight channels act as folding lines in the absorbent structure which contribute to provide a desirable bucket shape to the diaper once worn. The diaper once worn conforms to the inside of the wearer's tight. As a result, a U-like shape is achieved which minimizes leakage and increases comfort. These channels also improve fluid transportation within the absorbent structure and therefore contribute to fast insult acquisition.

Alternatively, the longitudinal main channels may be curved, as shown in FIG. 4B. Curved channels act as folding lines in the absorbent structure which assist the absorbent structure in following the morphology of the diaper's wearer, i.e. the channels constrain the product to take a U-like shape when the diaper is worn and compressed by the wearer's tights. Thus, the channels provide a comfortable and superior fit in addition to permitting improved liquid transportation.

The longitudinal main channels 26 may be oblique channels, as shown in FIG. 4C, i.e. straight channels oriented under an angle θ of up to 30 degrees, or up to 20 degrees, or up to 10 degrees with respect to the longitudinal central axis of the absorbent structure.

In some other alternatives, the longitudinal main channels may be angled channels, as shown in FIG. 4D. Angled channels are channels made of two or more portions connected under an angle σ to one another. Typically, angled channels are made of two portions connected under an angle σ of at least 150 degrees, or at least 160 degrees or at least 170 degrees.

In some embodiments, the longitudinal main channels may be so-called "ramified" channels, i.e. channels having at least one extremity which may not end with a straight, angled or curved transverse edge 28 but with a ramification 29. The ramification 29 may form an angle α of up to 30 degrees, or up to 20 degrees or up to 10 degrees with respect to the longitudinal central axis of the channel.

The longitudinal main channels 26 may have an average width w of from 3 mm to 15 mm, or from 4 mm to 14 mm or from 5 mm to 12 mm (the average width of a channel is the average distance between its longitudinal side edges 27). The average width of the longitudinal main channels may be at least 4% of the width of the absorbent layer, or at least 7% and up to 15%, or 20% or 25%. In some embodiments, the longitudinal main channels may have an average width w of from 3 mm to 18 mm, or from 5 mm to 15 mm or from 6 to 10 mm. The ramifications 29, as well, have an average width w of at least 3 mm or of at least 4% of the width of the absorbent layer, or of at least 7% and up to 15%, or up to 20% or up to 25% (average distance between the longitudinal edges 27' of the ramifications 29).

The longitudinal main channels 26 may be separated in the crotch region by a distance D (shown in FIG. 2) of at least 5%, or at least 10%, or at least 20%, or at least 25% of the transverse dimension (width) of the absorbent layer in said crotch region. It was found that when these two longitudinal main channels are separated by a distance of at least 5% of the transverse dimension of the absorbent layer in the crotch region, the disposable diaper takes a desirable bucket shape which improves the fit of the diaper. In some embodiments, the longitudinal main channels may be separated in the crotch region by a distance of at least 10 mm, or at least 15 mm, or at least 20 mm, or at least 30 mm. In some embodiments, the distance separating the longitudinal main channels in the crotch region is from 20 to 30 mm.

The inventors have found that when an absorbent structure is provided with at least two channels as described above, i.e. two longitudinal main channels, the flexibility of the absorbent structure is increased, especially for absorbent structure comprising exclusively absorbent polymer particles in the absorbent layer. The two channels create bending lines which drive the bending of the diaper to conform to the wearer's anatomy and therefore improve the fit of the diaper.

Furthermore, the inventors observed that absorbent structure having at least two channels as described above exhibit better fluid transportation versus absorbent structure of the same type not comprising channels. Indeed, it was observed that the channels provide for fast insults acquisition which reduces risk of leakages. The channels avoid saturation of the absorbent layer in the region of fluid discharge which increases the risk of leakages.

Secondary Channels

The absorbent layer may comprise further channels 26' to further increase the fluid transportation and/or fit of the absorbent article, referred herein as secondary channels. The above description of the longitudinal main channels may equally apply to any of said secondary channels 26'. However, in some embodiments, the secondary channels may be shorter than the main longitudinal channels.

The secondary channels may extend in the longitudinal dimension of the absorbent layer (longitudinal secondary channels) and/or in the transverse dimension of the absorbent layer (transverse secondary channels), provided they do not extend up to the longitudinal edges and/or transverse edges of the absorbent layer. Thus, the absorbent layer is free of channels, i.e. longitudinal main channels and secondary channels, extending up to its longitudinal edges and its transverse edges.

The longitudinal secondary channels may extend over a distance V' of at least 10%, or at least 15%, or at least 20% of the longitudinal dimension M of the absorbent layer (as shown in FIG. 6). They may extend up to 90% of the longitudinal dimension of the absorbent layer. Typically, the longitudinal secondary channels extend up to 30% or 45% of the longitudinal dimension of the absorbent layer.

Transverse secondary channels may extend over a distance of at least 10%, or at least 15%, or at least 20%, of the transverse dimension (width) N of the absorbent layer. They may extend up to 90% of the transverse dimension of the absorbent layer. Typically, the transverse secondary channels extend up to 30% or 45% of the transverse dimension of the absorbent layer. In some embodiments, the absorbent layer may not comprise transverse channels.

Typically, the secondary channels are distributed such that along each transverse edge of the absorbent layer and immediately adjacent to said edge, the strip which extends in the transverse dimension of the absorbent layer from one longitudinal edge to the other over a distance F' or G' remains free of channels (as disclosed above in respect of the longitudinal main channels distribution).

Typically, the secondary channels are distributed such that along each longitudinal edge and immediately adjacent to said edge, the strip which extends in the longitudinal dimension of the absorbent layer from one transverse edge to the other over a distance H' or I' remains free of channels (as disclosed above in respect of the longitudinal main channels distribution).

The longitudinal main channels and, when present, the secondary channels may be distributed in the absorbent layer such that a strip extending along the central longitudinal axis of the absorbent layer (and including said axis) from one transverse edge to the other one, and having a width D' of at least 5%, or at least 10% and up to 60%, or up to 70%, or up to 75% of the transverse dimension of the absorbent layer remains free of channels. The absorbent polymer particles may be continuously present in said strip. For example, said strip may have a width D' of at least 5 mm, or at least 10 mm, or at least 15 mm or 20 mm and up to 70 mm or up to 40 mm. The absence of channels in said strip is advantageous since it at least inhibits the diaper from taking an inverted V-shape configuration once worn. Inverted V-shape configuration increases the risk of fluid leakages. In some embodiments, the average basis weight of absorbent polymer particles in said strip is high, i.e. at least 350 gsm and up to 1000 gsm, or for example from 450 gsm to 750 gsm.

Although the secondary channels may be transverse secondary channels, the absorbent layer may not comprise any such channels in the crotch region. Channels extending in the transverse dimension in the crotch region would transport liquids to the transverse edges and would increase undesirably the risk of fluid leakages and/or run off. However, such secondary channels may be present in the front region and/or back region of the absorbent layer.

Longitudinal secondary channels may be present in the front region, back region and/or crotch region of the absorbent layer.

As disclosed in respect of the longitudinal main channels, the secondary channels may be straight channels parallel to the longitudinal central axis of the absorbent structure (as shown in FIG. 4A), curved channels (as shown in FIG. 4B), angled channels (as shown in FIG. 4D), oblique channels (as shown in FIG. 4C) or ramified channels (as shown in FIG. 4E). Oblique longitudinal channels, when present in the front or back region of the absorbent layer (i.e. not in the crotch region), may form an angle θ of up to 60 degrees, or up to 50 degrees, or up to 45 degrees with the longitudinal central axis of the absorbent layer.

The secondary channels may have an average width w' of from 3 mm to 15 mm, or from 4 mm to 14 mm or from 5 mm to 12 mm (the average width of a channel is the average distance between its longitudinal side edges 27) or the average width of the secondary channels may be at least 4% of the width of the absorbent layer, or at least 7% and up to 15%, or 20% or 25%. In some embodiments, the secondary channels may have an average width w' of from 3 mm to 18 mm, or from 5 mm to 15 mm or from 6 to 10 mm. The ramifications 29, as well, have an average width w' of at least 3 mm or of at least 4% of the width of the absorbent layer, or at least 7% and up to 15%, or up to 20% or up to 25% (average distance between the longitudinal edges 27' of the ramifications 29).

The longitudinal main channels and secondary channels may be spaced apart from each other by a distance of at least 5 mm, or at least 8 mm.

The absorbent layer may comprise one or more of said secondary channels, such as 2, 3, 4, 5 or 6. The absorbent layer may comprise an even number of secondary channels. The secondary channels may be distributed in the absorbent layer such that each longitudinal region of the absorbent layer comprises an equal number of secondary channels. In some embodiments, the longitudinal regions comprising the channels (i.e. main longitudinal channels and secondary channels) are mirror images of each other with respect to the central longitudinal axis of the absorbent layer.

In some embodiments, such as illustrated in FIGS. 3A to 3C, the longitudinal secondary channels and main longitudinal channels are not distinguishable, i.e. the longitudinal secondary channels and main longitudinal channels are similar. The resulting absorbent layer may thus be seen as comprising more than two longitudinal main channels 26 which are at least present in the crotch region (e.g. 4 longitudinal main channels). In some embodiments, it may be desired that the maximal number of channels in the crotch region is such that the sum of the widths w of the channels 26 is less than 50% of the transverse dimension (width) of the absorbent layer in the crotch region.

In some embodiments, such as shown in FIG. 5, the absorbent layer 17 may comprise two main longitudinal channels 26 as described above and two secondary longitudinal channels in the front region 26'. The two main longitudinal channels 26 are at least present in the crotch region. By at least present in the crotch region, it is meant that said two main longitudinal channels may extend up the front region and/or back region. The two main longitudinal channels 26 at least present in the crotch region may extend over a distance L which is at least 15% of the longitudinal dimension M of the absorbent layer. The secondary longitudinal channels 26' in the front region may extend over a distance V' which is at least 10% to 20% of the longitudinal dimension M of the absorbent layer. The two main longitudinal channels 26 in the crotch region may be curved channels whereas the two secondary longitudinal channels 26' in the front region may be oblique channels. The channels in one of the longitudinal regions may be mirror images of each other in the other longitudinal region.

In some other embodiments, such as shown in FIG. 6, the absorbent layer 17 may comprise two longitudinal main channels 26 in the crotch region, two longitudinal secondary channels 26' in the front region and two longitudinal secondary channels 26' in the back region. The longitudinal main channels 26 in the crotch region 25 may extend across at least 15% of the longitudinal dimension of the absorbent layer. The longitudinal secondary channels 26' in the front region and back region may extend over a distance V' which is at least 10% to 20% of the longitudinal dimension M of the absorbent layer. The longitudinal main channels 26 in the crotch region may be curved channels whereas the longitudinal secondary channels 26' in the front region and back region may be oblique channels. The channels in one of the longitudinal regions may be mirror images of each other in the other longitudinal region.

When the secondary channels 26' are longitudinal secondary channels extending in the crotch region, it may be desired that the maximal number of channels in the absorbent layer is such that the sum of the widths w and w' of the channels (secondary channels and main longitudinal channels) is less than 50% of the transverse dimension of the absorbent layer in the crotch region.

In some embodiment herein, it may be desired that the region 30 of the absorbent layer immediately adjacent the channels 26 and 26' and extending over a distance k of at least 3 mm, or of at least 5 mm, or of at least 7 mm from the edges of the channels comprises absorbent polymer particles present substantially continuously. In these regions 30, the average basis weight of absorbent polymer particles may be high, i.e. at least 350 gsm, or at least 400 gsm, or at least 500 gsm or at least 600 gsm.

Absorbent Layer

As explained above, channels 26 and 26' are regions free of absorbent polymer particles extending through the thickness of the absorbent layer. The absorbent layer comprises absorbent polymer particles 50 alone or in combination with other materials such as cellulose. The absorbent layer may comprise only absorbent polymer particles. The absorbent polymer particles are immobilized on the substrate layer, typically by a thermoplastic adhesive material 40.

Typically the absorbent polymer particles suitable for use in the absorbent layer can comprise any absorbent polymer particles known from superabsorbent literature, for example such as described in Modern Superabsorbent Polymer Technology, F. L. Buchholz, A. T. Graham, Wiley 1998.

The absorbent polymer particles may be spherical, spherical-like or irregular shaped particles, such as Vienna-sausage shaped particles, or ellipsoid shaped particles of the kind typically obtained from inverse phase suspension polymerizations. The particles can also be optionally agglomerated at least to some extent to form larger irregular particles.

The absorbent polymer particles can be selected among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in the PCT Patent Application WO 07/047598, WO 07/046052, WO2009/155265 and WO2009/155264.

The absorbent polymer particles may be internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as crosslinkers described in WO2009/155265.

The absorbent polymer particles may be externally cross-linked (post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502,bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

The absorbent polymer particles may have surface modifications, such as being coated or partially coated with a coating agent. Examples of coated absorbent polymer particles are disclosed in WO2009/155265. The coating agent may be such that it renders the absorbent polymer particles more hydrophilic. The coating agent may be a polymer, such as an elastic polymer or a film-forming polymer or an elastic film-forming polymer, which forms an elastomeric (elastic) film coating on the particle. The coating may be a homogeneous and/or uniform coating on the surface of the absorbent polymer particles. The coating agent may be applied at a level of from 0.1% to 5%, or from 0.2% to 1% by weight of the surface-modified absorbent polymer particles.

Typically, the absorbent polymer particles may have a selected particle size distribution. For example, the absorbent polymer particles may have a particle size distribution in the range from 45 µm to 4000 µm, more specifically from 45 µm to about 1000 µm, or from about 100 µm to about 850 µm, or from about 100 µm to about 600 µm. The particle size distribution of a material in particulate form can be determined as it is known in the art, for example by means of dry sieve analysis (EDANA 420.02 "Particle Size distribution). Optical methods, e.g. based on light scattering and image analysis techniques, can also be used.

The absorbent layer of the absorbent structure may comprise absorbent polymer particles, and optionally cellulose, distributed on the substrate layer such as to form as a continuous layer, i.e. an uninterrupted layer of absorbent polymeric particles and cellulose when present, which nevertheless comprises regions substantially free of absorbent polymer particles. These discrete regions substantially free of absorbent particles correspond to the channels of the absorbent structure. In some embodiments, the absorbent layer is cellulose free. Alternatively, the absorbent layer may comprise absorbent polymer particles, and optionally cellulose, distributed on the substrate layer such as to form a discontinuous layer. In some embodiments, the absorbent layer is cellulose free. In these embodiments, the absorbent polymer particle and cellulose when present, may be deposited on the substrate layer in clusters of particles (and cellulose when present), thus forming a discontinuous layer or an interrupted layer of absorbent polymer particles (and cellulose when present) which nevertheless comprises regions substantially free of clusters of absorbent polymer particles. These discrete regions substantially free of clusters of absorbent particles correspond to the channels of the absorbent structure. The clusters of absorbent polymer particles (and cellulose when present) may have a variety of shape including, but not limited to, circular, oval, square, rectangular, triangular and the like. Suitable methods for depositing particles in cluster of particles are disclosed in EP 1621167 A2, EP 1913914 A2 and EP 2238953 A2. Typically, absorbent polymer particles are deposited on the substrate layer in clusters of particles when two such absorbent structures are combined to form an absorbent core. The two absorbent structures are combined such that the resulting absorbent core comprises absorbent polymer particles substantially continuously distributed between the two substrate layers, except in regions where channels are present. "Substantially continuously distributed" as used herein indicates that the first substrate layer and second substrate layer are separated by a multiplicity of absorbent polymer particles. It is recognized that there may be minor incidental contact areas between the first substrate layer and second substrate layer within the absorbent particulate polymer material area (i.e. area between the two substrate layers). Incidental contact areas between the first substrate and second substrate may be intentional or unintentional (e.g. manufacturing artifacts) but may not form geometries such as pillows, pockets, tubes, quilted patterns and the like.

The absorbent polymer particles may be immobilized on the substrate layer. Immobilization may be achieved by applying a thermoplastic adhesive material which holds and immobilizes the absorbent polymer particles, and cellulose when present, on the substrate layer. Some thermoplastic adhesive material may also penetrate into the layer of absorbent polymer particles and into the substrate layer to provide further immobilization and affixation. The thermoplastic adhesive material may not only help in immobilizing the absorbent polymer particles on the substrate layer but also helps in maintaining the integrity of the channels. The thermoplastic adhesive material avoids that a significant amount of absorbent polymer particles migrates into the channels.

Integrity/immobilization of the channels may also be achieved by allowing the substrate layer supporting the absorbent polymer particles to fold into the channels, i.e. undulate into the channels. Alternatively, integrity/immobilization may be achieved by allowing a further substrate layer, such as the core cover when present, to fold into the channels, i.e. undulate into the channels. When two absorbent structures as disclosed above are combined, integrity/immobilization may be achieved by allowing the substrate layer of one of the absorbent structures to fold into the channels. In some embodiments, an adhesive (e.g. a thermoplastic adhesive material) may be applied on these portions of the substrate layer which undulates into the channels to provide further affixation.

The thermoplastic adhesive material may be applied as a continuous layer (i.e. uniformly) over the absorbent layer. In some embodiments, the thermoplastic adhesive material contacts the absorbent polymer particles (and cellulose when present) and part of the substrate layer when the absorbent polymer particles (and cellulose when present) are deposited in clusters.

In some embodiments, the thermoplastic adhesive material may be applied as a fibrous layer forming a fibrous network over the absorbent layer. The thermoplastic adhesive fibrous layer may be at least partially in contact with the absorbent polymer particles (and cellulose when present) and partially in contact with the substrate layer of the absorbent structure when the absorbent polymer particles (and cellulose when present) are deposited in clusters. Thereby, the thermoplastic adhesive material may provide cavities to cover the absorbent polymer particles, and thereby immobilizes this material and the channels when present.

Thermoplastic adhesive materials suitable for immobilizing the absorbent polymer particles typically combine good cohesion and good adhesion behavior. Good adhesion promotes good contact between the thermoplastic adhesive material and the absorbent polymer particles and the substrate layer. Good cohesion reduces the likelihood that the adhesive breaks, in particular in response to external forces, and namely in response to strain. When the absorbent structure/core absorbs liquid, the absorbent polymer particles swell and subject the thermoplastic adhesive material to external forces. The thermoplastic adhesive material may allow for such swelling, without breaking and without imparting too many compressive forces, which would restrain the absorbent polymer particles from swelling.

Thermoplastic adhesive materials suitable for use in the present disclosure includes hot melt adhesives comprising at least a thermoplastic polymer in combination with a plasticizer and other thermoplastic diluents such as tackifying resins and additives such as antioxidants. Example suitable hot melt adhesive materials are described in EP 1447067 A2. In some embodiments, the thermoplastic polymer has a molecular weight (Mw) of more than 10,000 and a glass transition temperature (Tg) below room temperature or $-6°$ C.>Tg<16° C. In certain embodiments, the concentrations of the polymer in a hot melt are in the range of about 20 to about 40% by weight. In certain embodiments, thermoplastic polymers may be water insensitive. Example polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The thermoplastic adhesive material, typically a hot-melt adhesive material, is generally present in the form of fibres, i.e. the hot melt adhesive can be fiberized. In some embodiments, the thermoplastic adhesive material forms a fibrous network over the absorbent polymer particles. Typically, the fibres can have an average thickness from about 1 µm to about 100 µm, or from about 25 µm to about 75 µm, and an average length from about 5 mm to about 50 cm. In particular the layer of hot melt adhesive material can be provided such as to comprise a net-like structure. In certain embodiments the thermoplastic adhesive material is applied at an amount of from 0.5 to 30 $g/m^2$, or from 1 to 15 $g/m^2$, or from 1 and 10 $g/m^2$ or even from 1.5 and 5 $g/m^2$ per substrate layer.

A typical parameter for a hot melt adhesive suitable for use in the present disclosure can be a loss angle tan Delta at 60° C. of below the value of 1, or below the value of 0.5. The loss angle tan Delta at 60° C. is correlated with the liquid character of an adhesive at elevated ambient temperatures.

The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

It may be beneficial, e.g. for process reasons and/or performance reasons, that the thermoplastic adhesive material has a viscosity of between 800 and 4000 mPa·s, or from 1000 mPa·s or 1200 mPa·s or from 1600 mPa·s to 3200 mPa·s or to 3000 mPa·s or to 2800 mPa·s or to 2500 mPa·s, at 175° C., as measurable by ASTM D3236-88, using spindle 27, 20 pmp, 20 minutes preheating at the temperature, and stirring for 10 min.

The thermoplastic adhesive material may have a softening point of between 60° C. and 150° C., or between 75° C. and 135° C., or between 90° C. and 130° C., or between 100° C. and 115° C., as can be determined with ASTM E28-99 (Herzog method; using glycerine).

In one embodiment herein, the thermoplastic adhesive component may be hydrophilic, having a contact angle of less than 90°, or less than 80° or less than 75° or less than 70°, as measurable with ASTM D 5725-99.

In some embodiments, the absorbent structure may also comprise an adhesive material deposited on the substrate before application of the absorbent polymer particles on the substrate layer, referred herein as the auxiliary adhesive. The auxiliary adhesive may enhance the immobilization of the absorbent polymer particles on the substrate layer. It may be a thermoplastic adhesive material, and comprise the same thermoplastic adhesive material as described hereinabove or it may be different. An example of commercially available adhesive is H. B. Fuller Co. (St. Paul, Minn.) Product No. HL-1620-B. The thermoplastic adhesive material may be applied to the substrate layer by any suitable means.

In some embodiments, the absorbent polymer particles, and optionally cellulose, may be distributed evenly in the longitudinal and/or transverse dimensions of the absorbent layers irrespective of whether the absorbent layer is a continuous layer or a discontinuous layer of absorbent polymer particles, and optionally cellulose, as described above to provide an absorbent core having an even distribution of absorbent polymer particles. The average basis weight of absorbent polymer particles may depend on the particular diaper in which it may be incorporated. In some embodiments, the average basis weight of absorbent polymer particles in the absorbent core may be from 350 gsm to 1500 gsm. The amount of absorbent polymeric particles in the respective region is calculated by determining the weight of absorbent polymeric material in this region and dividing it by the total surface area of the region (hence, the average amount is taken).

In some embodiments, the absorbent polymer particles, and optionally cellulose, may be distributed unevenly in the longitudinal and/or transverse dimension of at least one of the absorbent layers to provide a profiled absorbent core. For example, the crotch region of the absorbent structure/core may comprise a higher amount of absorbent polymer particles per area compared to the front and back regions of the absorbent structure/core. In some embodiment, the front half of the absorbent core comprises most of the absorbent capacity, i.e. it may comprise more than about 60% of the absorbent polymer particles, or more than about 65%, or more than 70%, based on the total weight of absorbent polymer particles in the absorbent core.

In some embodiments, the absorbent structure as disclosed above may form the absorbent core of the disposable diaper or may be a component thereof (i.e. the absorbent core may be a laminate of absorbent structures).

The absorbent core may further comprise a cover layer, typically disposed on the thermoplastic adhesive material. The cover layer may be a separate layer or it may be unitary with the substrate layer. In such a case, the substrate layer supporting the absorbent polymer particles is folded to form a top and bottom layer which encloses the absorbent polymer particles. The cover layer may be provided of the same material as the substrate layer, or may be provided of a different material. The layers may be bonded together at about the periphery to enclose the absorbent polymer particles therein, e.g. by adhesive bonding and/or heat bonding. In some embodiments, the core cover may undulate into the channels.

In some embodiments, the absorbent core may comprise an acquisition system which is disposed between the topsheet and the wearer facing side of the absorbent structure. The acquisition system may serve as a temporary reservoir for liquid until the absorbent structure can absorb the liquid. The acquisition system may comprise a single layer or multiple layers, such as an upper acquisition layer facing towards the wearer's skin and a lower acquisition layer facing the garment of the wearer. The acquisition system may be in direct contact with the absorbent structure. In these embodiments, the acquisition system may fill in the channels or part thereof. In some embodiments, the acquisition system may be placed on top of the core cover when present. In embodiments wherein the core cover or substrate layer folds into the channels, i.e. undulates into the channels, the acquisition system may fill in the channels or part thereof. In some embodiments, the acquisition system, or one layer thereof, may be bonded to the core cover or substrate layer which undulates into the channels thus providing an undulating profile to said acquisition system.

In a certain embodiment, the acquisition system may comprise chemically cross-linked cellulosic fibers. Such cross-linked cellulosic fibers may have desirable absorbency properties. Example chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an example cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers may comprise a non-woven, which may be hydrophilic. Further, according to a certain embodiment, one or both of the upper and lower acquisition layers may comprise the chemically cross-linked cellulosic fibers, which may or may not form part of a nonwoven material. According to an example embodiment, the upper acquisition layer may comprise a nonwoven, without the cross-linked cellulosic fibers, and the lower acquisition layer may comprise the chemically cross-linked cellulosic fibers. Further, according to an embodiment, the lower acquisition layer may comprise the chemically cross-linked cellulosic fibers mixed with other fibers such as natural or synthetic polymeric fibers. According to example embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. Suitable non-woven materials for the upper and lower acquisition layers include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

In some embodiments, as shown in FIGS. 7 to 10, the absorbent core of the disposable diaper may comprise two or more absorbent structures as disclosed herein, i.e. absorbent structures which comprise channels, which are combined or superposed. Typically, the absorbent structures may be combined such that the thermoplastic adhesive material of the first absorbent structure directly contacts the thermoplastic adhesive material of the second absorbent structure.

Figure 7:
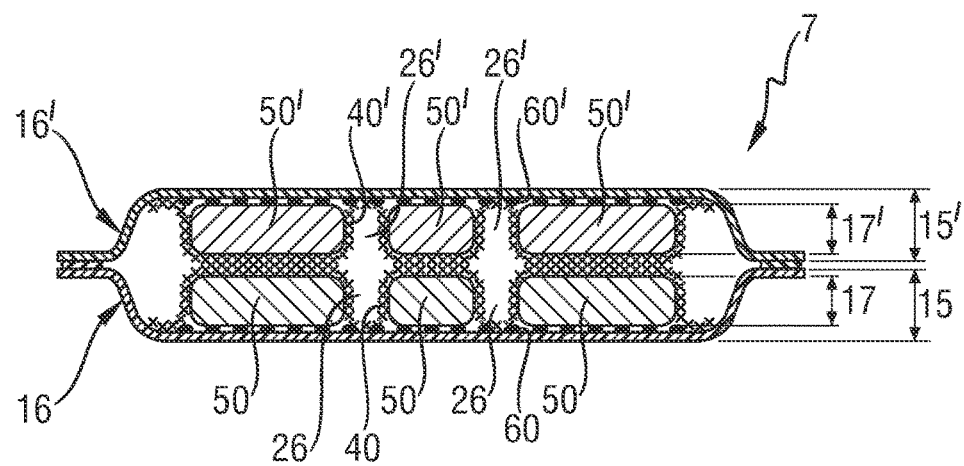
FIGS. 7 to 13 are schematic cross-sections of an absorbent core taken in the transverse dimension in accordance with various non-limiting embodiments.
Figure 8:
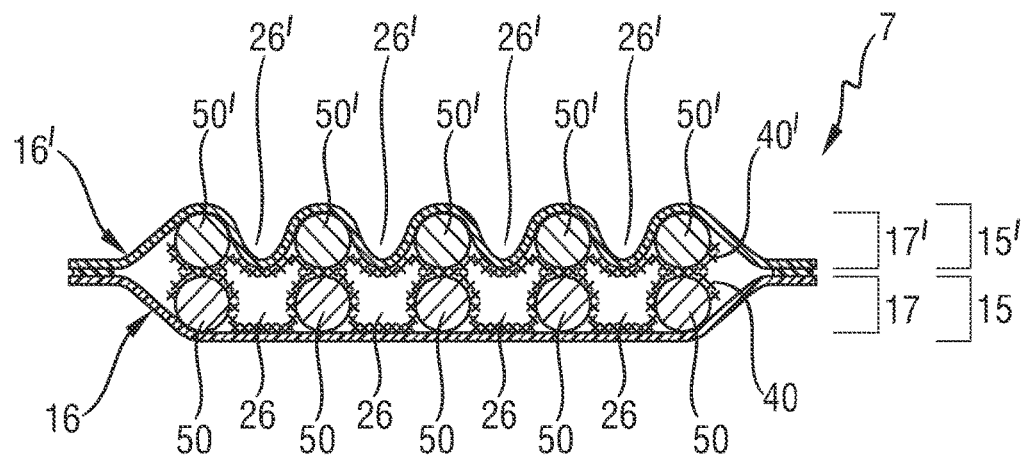
Figure 9:
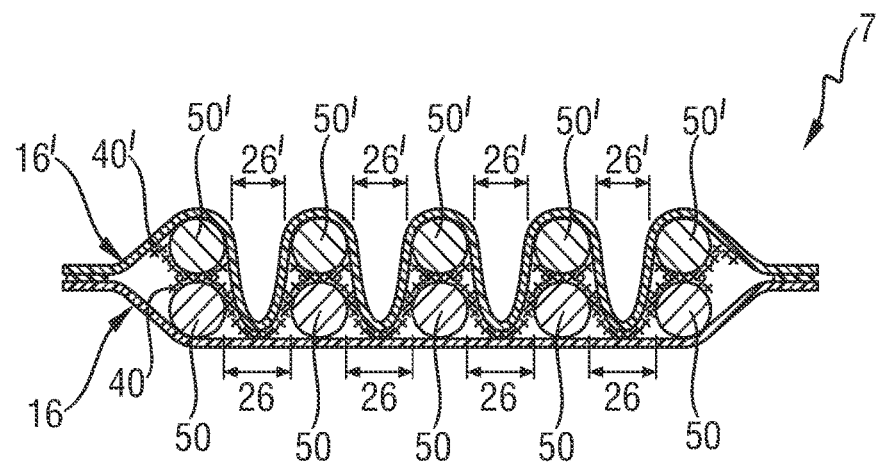
Figure 10:
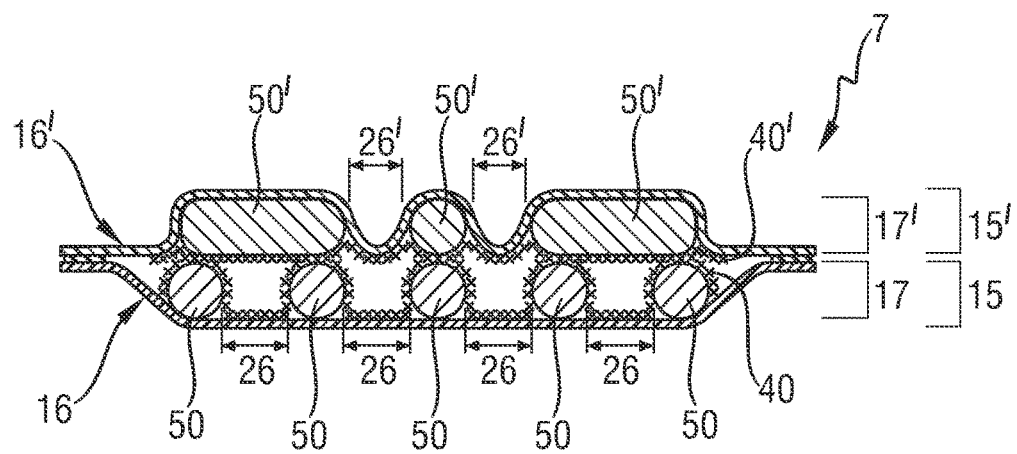

FIGS. 7, 8, 9 and 10 illustrate embodiments wherein a first absorbent structure 15 comprising an absorbent layer 17 with channels 26 is combined with a second absorbent structure 15' comprising an absorbent layer 17' with channels 26'. In the shown embodiments, the thermoplastic adhesive material 40 of the first absorbent structure directly contacts the thermoplastic adhesive material 40' of the second absorbent structure. An auxiliary adhesive 60 may be present on the substrate layer of the first and/or second absorbent structure for further immobilization of the absorbent polymer particles (as shown in FIG. 7). In some embodiments, the substrate layer 16' of the second absorbent structure 15' may undulate into the channels 26' of the second absorbent structure (as shown in FIGS. 8 and 10) and even into the channels 26 of the first absorbent structure 15, where it can be possibly adhered to the substrate layer 16 of the first absorbent structure (as shown in FIG. 9). Typically, when the substrate layer of one absorbent structure undulates into the channels, the substrate layers of the two absorbent structures are not coextensive, i.e. one of the substrate layer may be wider or longer to penetrate into the channels 26 and/or 26'. Undulations of the substrate layer into the channels contribute to the integrity of the channels in dry and wet states.

In embodiments wherein the two or more absorbent structures comprise channels, it may be that the first and second absorbent structures are mirror images of each other. In these embodiments, the channels 26 of the first absorbent structure 15 substantially superpose the channels 26'of the adjacent second absorbent structure 26', as shown in FIGS. 7, 8 and 9. The resulting absorbent core is a laminate of absorbent structures 17 and 17' with channels extending substantially through the thickness of the absorbent core (by substantially as used herein it is meant that the thicknesses of the substrate layers are hereby neglected).

In embodiments wherein the two or more absorbent structures comprise channels, the first and second absorbent structures may be different. In some of these embodiments, some of the channels of the two absorbent layers may superpose (as shown in FIG. 10). In other embodiments, the channels of one absorbent structure may not superpose the channels of the adjacent absorbent structure but are complementary with the channels of the adjacent structure. By complementary it is meant that the channels of the second absorbent structure form an extension of the channels of the first absorbent structure.

Figure 11:
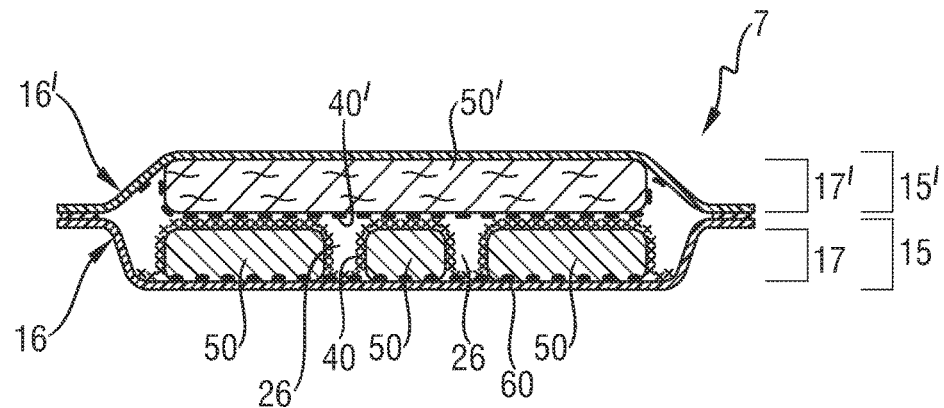
Figure 12:
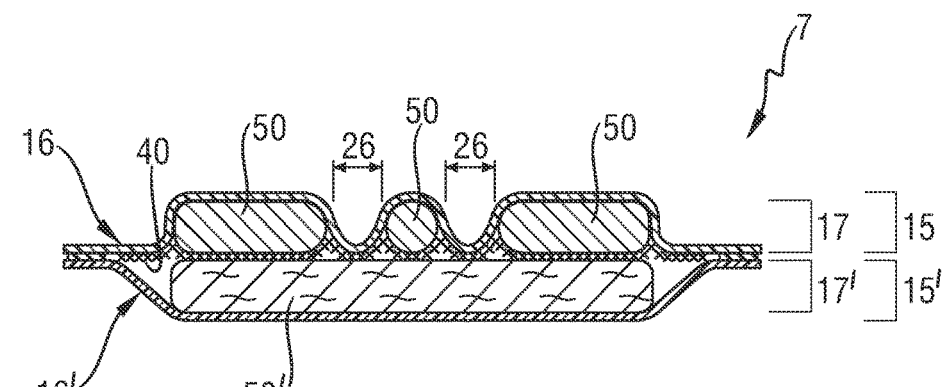
Figure 13:
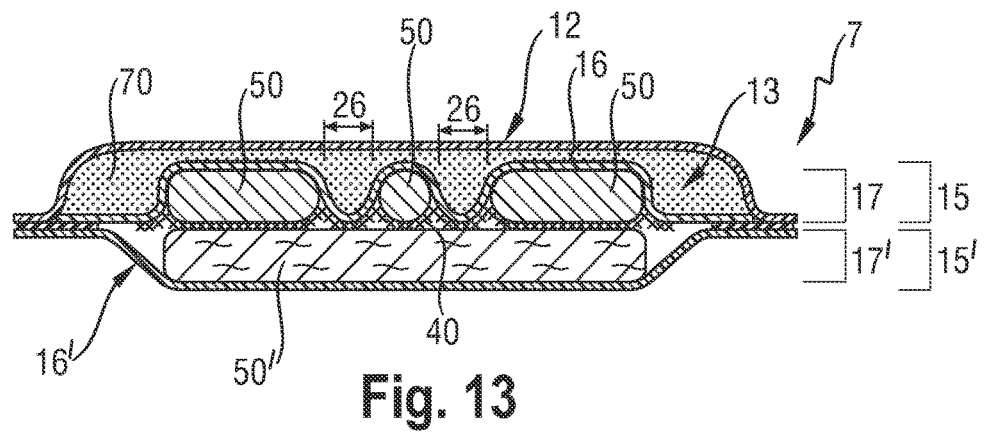
Figure 14:
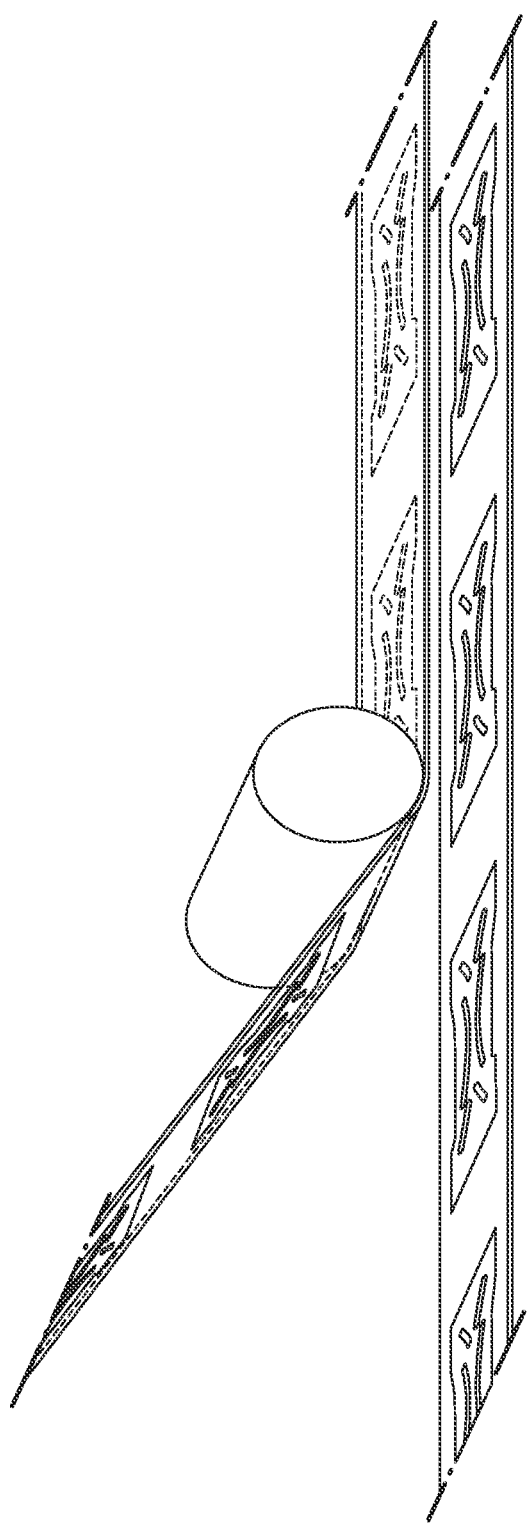
FIG. 14 is a schematic representation of a process for making an absorbent structure comprising an absorbent layer with channels in accordance with one non-limiting embodiment.

In some embodiments, as shown in FIGS. 11 to 13, the absorbent core of the disposable diaper may comprise one or more absorbent structures as disclosed herein, combined with an absorbent structure comprising an absorbent layer which is free of channels. In these embodiments, the absorbent structure free of channels comprises a substrate layer and an absorbent layer as disclosed which is however free of channels. When only one of the absorbent structures comprises said channels, the absorbent structure with channels may in some embodiments herein be closer to the wearer in use than the absorbent structure(s) without channels.

FIGS. 11, 12 and 13 illustrate embodiments wherein a first absorbent structure 15 with channels 26 is combined with a second absorbent structure 15' free of channels. In the embodiment shown in FIG. 11, the thermoplastic adhesive material 40 of the first absorbent structure 15 directly contacts the thermoplastic adhesive material 40' of the second absorbent structure 15' whereas in FIGS. 12 and 13, the second absorbent structure 15' may not comprise any such thermoplastic adhesive material 40' (however, it may be present to immobilize the absorbent layer on the substrate layer). An auxiliary adhesive 60 may be present on the substrate layer of the first and/or second absorbent structure for further immobilization of the absorbent polymer particles 50 (as shown in FIG. 11). In some embodiments, the substrate layer 16 of the first absorbent structure 15 may undulate into the channels 26 of the first absorbent structure (as shown in FIGS. 12 and 13). The absorbent core may further comprise an acquisition system 70 that penetrates and fill in the channels (however in some embodiments, the acquisition system may not fill in the channels). FIG. 13 shows an embodiment wherein the acquisition system 70 comprises a first layer 12 and second layer 13, wherein the second layer fills in the channels.

Method of Making the Absorbent Structure

The absorbent structure having channels herein may be made by any method comprising the step of depositing absorbent polymer particles and optionally cellulose to form an absorbent layer onto a substrate layer, for example by placing first said substrate layer onto raised portions in the shape and dimensions of said channels to be produced and then depositing said absorbent polymer particles and optionally cellulose thereon; thereby, the absorbent polymer particles and optionally cellulose may not remain onto said raised portions, but only on the remaining portions of the substrate layer.

The absorbent structure free of channels herein may be made by any method comprising the step of depositing absorbent polymer particles and optionally cellulose as an absorbent layer on a substrate layer.

In some embodiments, the absorbent structure with the substrate layer with therein two or more channels with substantially no absorbent material is for example obtainable by a method comprising the steps of:
a) providing a feeder for feeding said absorbent material (absorbent polymer particles and optionally cellulose) to a first moving endless surface, such as a hopper;
b) providing a transfer means for transferring a substrate layer to a second moving endless surface;
c) providing a first moving endless surface, having one or more absorbent layer-forming reservoirs with a longitudinal dimension and averaged length, a perpendicular transverse dimension and average width, and, perpendicular to both, a depth dimension and average depth, and a void volume for receiving said absorbent material therein, said reservoir(s) comprising one or more substantially longitudinally extending raised strips, not having a void volume, for example each having an average width W of at least 4% or at least 5% of the average width of the reservoir, and an average length L of at least 5% and at the most 30% of the average longitudinal dimension of the reservoir; said reservoir(s) being for transferring said absorbent material to said second moving endless surface adjacent and in proximity thereto;

d) providing a second moving surface, having an outer shell that has one or more air permeable or partially air permeable receptacles with for receiving said substrate layer thereon or therein, with a receiving area and with one or more substantially longitudinally extending mating strips that may be air impermeable, and having each an average width of for example W' of at least 2.5 mm, optionally from 0.5×W to 1.2×W, an average length of for example L' being from about 0.8×L to 1.2×L;

whereby said air-permeable outer shell is connected to one or more secondary vacuum systems for facilitating retention of the substrate layer and/or said absorbent material thereon, and whereby, in a meeting point, said first moving endless surface and said outer shell are at least partially adjacent to one another and in close proximity of one another during transfer of said absorbent material and such that each mating strip is substantially completely adjacent and in close proximity to a raised strip during transfer of said absorbent material;

e) feeding with said feeder an absorbent material to said first moving endless surface, in at least said reservoir (s) thereof;

f) optionally, removing any absorbent material on said raised strips (s);

g) simultaneously, transferring said substrate layer to said second moving endless surface, onto or into said receptacle(s);

h) selectively transferring in said meeting point, said absorbent material with said first moving endless surface only to said part of the supporting sheet that is on or in said receiving area of said receptacle.

Said reservoir(s) may be formed by of a multitude of grooves and/or cavities with a void volume, for receiving said absorbent material therein. In some embodiments, the average width W of (each) strip may be at least 6 mm, or for example at least 7 mm, and/or at least at least 7%, or for example at least 10% of the average width of the respective reservoir.

Said grooves and/or cavities may each for example have a maximum dimension in transverse direction which is at least 3 mm, and whereby the shortest distance between directly neighboring cavities and/or grooves in substantially transverse dimension, is less than 5 mm. Cavities and/or grooves that are directly adjacent a raised strip may have a volume that is more than the volume of one or more, or all of their neighboring cavities or grooves, that are not directly adjacent said strip or another strip (thus further removed from a strip).

Said first moving endless surface's reservoir may be at least partially air permeable and said first moving endless surface may have a cylindrical surface with said reservoirs, rotatably moving around a stator, comprising a vacuum chamber; said second moving surface's outer shell may be cylindrical, rotatably moving around a stator, comprising a secondary vacuum chamber connected to said secondary vacuum system.

The method further comprises the step of i) applying an adhesive material to the absorbent structure of step h; and optionally applying an adhesive material (i.e. a second adhesive material) to said substrate layer, prior to step f, or simultaneously therewith, but in any event prior to step g).

Step i) 1) may involve straying said first adhesive material in the form of fibers onto said absorbent layer, or part thereof, for example substantially continuously, so it is also present in said channels.

Step i) 2) may involve slot coating or spray-coating the supporting sheet, either continuously, or for example in a pattern corresponding to the channel pattern. An absorbent structure obtained by said method can then be combined with an absorbent structure free of channels or with another absorbent structure made by this method to provide an absorbent core.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper having a transverse and longitudinal dimension, the disposable diaper comprising a backsheet, a topsheet and an absorbent core disposed therebetween, wherein the absorbent core comprises a first absorbent structure and a second absorbent structure to form a laminate, wherein each of the first absorbent structure and the second absorbent structure has a wearer-facing surface and a garment-facing surface comprising a substrate layer and an absorbent layer, wherein each absorbent layer comprises absorbent polymer particles and is cellulose free, supported by, and immobilized on the substrate layer, each absorbent layer comprising:

i. transverse and longitudinal dimensions;

ii. a pair of opposing longitudinal edges extending in the longitudinal dimension;

iii. a pair of opposing transversal edges extending in the transverse dimension;

iv. front, crotch and back regions arranged sequentially in the longitudinal dimension; and v. two longitudinal portions delimited by a plane having a dimension that is coextensive with a central longitudinal axis of the absorbent structure and a second dimension that is perpendicular to both the central longitudinal axis and a central transverse axis;

wherein each absorbent layer comprises at least two channels, each channel being substantially free of the absorbent polymer particles and each channel extending through the thickness of the absorbent layer in the longitudinal dimension, wherein each longitudinal portion of the absorbent layer comprises one of the channels, and wherein each of the channels:

a. has a width of at least 4% of the transverse dimension of the absorbent layer;

b. extends over at least 15% of the longitudinal dimension of the absorbent layer; and c. is at least present in the crotch region or part thereof;

provided each absorbent layer does not comprise channels substantially free of absorbent polymer particles extending in the transverse dimension of the absorbent layer in the crotch region and does not comprise channels substantially free of absorbent polymer particles extending up to the longitudinal and transversal edges of the absorbent layer;

wherein the absorbent core comprises an acquisition system which is disposed between the topsheet and the wearer-facing surface of the absorbent structure, and wherein the acquisition system is in direct contact with the first absorbent structure such that the acquisition system at least partially fills in the at least two channels of the first absorbent structure;

wherein the distance between two of the at least two channels in the crotch region is at least 5% of the transverse dimension of the absorbent layer in the crotch region and wherein the distance between the two of the at least two channels is from about 20 mm to about 30 mm in the crotch region.

2. The disposable diaper according to claim 1, wherein each of the at least two channels extend up to 90% of the longitudinal dimension of the absorbent layer.

3. The disposable diaper according to claim 1, wherein the first absorbent structure comprises one or more further channels substantially free of absorbent polymer particles extending through the thickness of the absorbent layer in the longitudinal or transverse dimension of said absorbent layer, and wherein said one or more further channels have a width of at least 3 mm.

4. The disposable diaper according to claim 3, wherein the one or more further channels are distributed in any of the front region and the back region of the absorbent layer.

5. The disposable diaper according to claim 3, wherein the one or more further channels are longitudinal channels.

6. The disposable diaper according to claim 3, wherein any of the one or more further channels are straight channels, oblique channels, curved channels or angled channels.

7. The disposable diaper according to claim 1, wherein the substrate layer of the first absorbent structure and the substrate layer of second absorbent structure are mirror images of each other and are combined such that at least one channel of the absorbent layer of the second absorbent structure superposes at least one channel of the absorbent layer of the first absorbent structure to form one or more channels through the thickness of the laminate.

8. The disposable diaper according to claim 7, wherein the substrate layer of the first absorbent structure is bonded to a substrate layer sheet of the second absorbent structure in the one or more channels.

9. The disposable diaper according to claim 1, wherein the substrate layer of one of the first and second absorbent structures undulates into one or more channels.

10. The disposable diaper according to claim 1, wherein one or more channels have a width of from 6 mm to 10 mm.

11. The disposable diaper according to claim 1, wherein the absorbent polymer particles are immobilized by a thermoplastic adhesive material on the substrate layer.

* * * * *